(12) United States Patent
Hansson et al.

(10) Patent No.: US 8,568,999 B2
(45) Date of Patent: Oct. 29, 2013

(54) DIAGNOSIS AND TREATMENT OF PREECLAMPSIA

(75) Inventors: Stefan Hansson, Lomma (SE); Bo Akerstrom, Lund (SE)

(73) Assignee: A1M Pharma AB, Lund (SE)

( * ) Notice: Subject to any disclaimer, the term of this patent is extended or adjusted under 35 U.S.C. 154(b) by 193 days.

(21) Appl. No.: 12/526,941

(22) PCT Filed: Feb. 12, 2008

(86) PCT No.: PCT/EP2008/001051
§ 371 (c)(1),
(2), (4) Date: Nov. 23, 2009

(87) PCT Pub. No.: WO2008/098734
PCT Pub. Date: Aug. 21, 2008

(65) Prior Publication Data
US 2010/0105070 A1    Apr. 29, 2010

(30) Foreign Application Priority Data
Feb. 12, 2007 (SE) ........................ 0700339

(51) Int. Cl.
*G01N 33/00* (2006.01)
(52) U.S. Cl.
CPC ...................... *G01N 33/00* (2013.01)
USPC ............................ 435/7.92; 435/7.1; 436/501

(58) Field of Classification Search
None
See application file for complete search history.

(56) References Cited

FOREIGN PATENT DOCUMENTS

| | | |
|---|---|---|
| SU | 1337778 A1 | 9/1987 |
| WO | 2003021275 A1 | 3/2003 |
| WO | 2005093413 A2 | 10/2005 |
| WO | 2007/082757 A2 | 7/2007 |

OTHER PUBLICATIONS

Rucknagel et al., Immunologic studies of hemoglobins: III. fetal hemoglobin changes in the circulation of pregnant women, Blood, vol. 10, 1955, pp. 1092-1099.*
Moscoso, H. et al. "Monoclonal Antibody to the g Chain of Human Fetal Hemoglobin Used to Develop and Enzyme Immunoassay", Clin. Chem. 1989, vol. 35, No. 10, pp. 1624-1628.
Al-Mufti, Raghad et al. "Increase fetal erythroblasts in women who subsequently develop pre-eclampsia", Human Reproduction, 2000, vol. 15, No. 7, pp. 1624-1628.
Sheridan, BL., et al., "The patterns of fetal haemoglobin production in leukaemia", British Journal of Haematology, vol. 34, No. 4, pp. 487-506 (1976).
Holzegreve W et al., "Fetal cells in cervical mucus and maternal blood" Bailliere's Best Practice and Research Clinical Obstetrics and Gynaecology, Bailliere Tindall, Londaon, GB, vol. 14, No. 4, 2000, p. 709-722.
Rayman Margaret P et al., "Abnormal iron parameters in the pregnancy syndrome preeclampsia." American Journal of Obstetrics and Gynecology, vol. 187, No. 2, Aug. 2002, pp. 412-418.
Cotton Frederic et al., "Evaluation of a capillary electrophoresis method for routine determination of hemoglobins A2 and F" Clinical Chemistry, vol. 45, No. 2, Feb. 1999, pp. 237-243.
Lafferty John D et al., "Evaluation of a dual hemoglobin A(2)/A(Ic) quantitation kit on the bio-rad variant II automated hemoglobin analyzer." Archives of Patholgy & Laboratory Medicine, Dec. 2002, vol. 126, No. 12, pp. 1494-1500.
Hubel Carl A et al., "Decreased transferrin and increased transferrin saturation in sera of women with preeclampsia: Implication ofor oxidative stress" American Journal of Obstetrics and Gynecology, vol. 175, No. 3 part 1, 1996, pp. 692-700.
Pepple D J et al., "Fetal haemoglobin level in pre-eclampsia." The West Indian Medical Journal, Mar. 2006, vol. 55, No. 2, Mar. 2006 p. 130.
Omu Alexander E et al., "Connection between human leucocyte antigens D region and T helper cytokines in preeclampsia." Archives of Gynecology and Obstetrics, vol. 269, No. 2, Jan. 2004, pp. 79-84.
Cai H et al., "Flow Cytometry-Based Minisequencing: A New Platform for High-Throughput Single-Nucleotide Polymorphism Scoring" Genomics, Academic Press, San Diego, US, vol. 66, No. 2, Jun. 1, 2000, pp. 135-143.
H. Yoshida et al., "Generation of Monoclonal Antibodies Specific for Human Hemoglobin", Agric. Biol. Chem., 52(11), pp. 2837-2841 (1988).
M. Allhorn et al., "Processing of the lipcalin alpha 1-microglobulin by hemoglobin induces heme-binding and heme-degradation properties", Blood, 99(6), pp. 1894-1901 (2002).
T. Berggard et al., "Histologic Distribution and Biochemical Properties of alpha 1-Microglobulin in Human Placenta", American Journal of Reproductive Immunology, vol. 41, pp. 52-60 (1999).

* cited by examiner

*Primary Examiner* — Gary W Counts
(74) *Attorney, Agent, or Firm* — Edwards Wildman Palmer LLP; Peter F. Corless; Christine C. O'Day

(57) ABSTRACT

The present invention relates to biomarkers for preeclampsia as well as treatment of this disease. In particular, the invention relates to methods for diagnosis or aiding in the diagnosis of preeclampsia of a pregnant female mammal to detect elevated levels of free haemoglobin, particularly free fetal haemoglobin. This facilitates and makes possible early diagnosis and clinical intervention when a preeclamptic condition is found. In addition, the invention relates to a method to treat female mammals with preeclampsia with the purpose to reverse the pathological conditions associated with this disease.

6 Claims, 21 Drawing Sheets

A    B    C

DIAGNOSIS AND TREATMENT OF PREECLAMPSIA

FIELD OF THE INVENTION

The present invention relates to biomarkers for preeclampsia as well as treatment of this disease. In particular, the invention relates to methods for diagnosis or aiding in the diagnosis of preeclampsia of a pregnant female mammal to detect elevated levels of particular substances. This facilitates and makes possible early diagnosis and clinical intervention when a preeclamptic condition is found. In addition, the invention relates to a method to treat female mammals with preeclampsia with the purpose to reverse the pathological conditions associated with this disease.

BACKGROUND OF THE INVENTION

Preeclampsia (PE), gestational proteinuric hypertension, complicates 3-7% of all pregnancies, and is a multisystem maternal disorder. Yearly 8,500,000 cases are reported worldwide, of which 5,000 are in Sweden. It is today the most common cause of death for both children and mothers during pregnancy.

PE has been named the disease of theories [Roberts, 2001] and was described as early as 3000 years ago by the ancient Egyptians [Stevens, 1975]. PE is still one of the dominating obstetric complications that cause perinatal and maternal morbidity and mortality. Clinical manifestations, i.e. hypertension and proteinuria, appear from 20 weeks of gestation onwards, but the underlying mechanisms may begin as early as at the time of implantation. As the disease progresses, angiospasmus in the brain and brain oedema may cause severe epileptic seizures—eclampsia [Lipstein et al., 2003].

The etiology for PE is still unknown; however recent data suggest that the disease evolves in two stages:

Stage 1. During placentation, a defect invasion of the placental cells, trophoblasts, into the muscle layers of the spiral arteries has been shown [Brosens et al., 2002; Page, 1939]. A growing body of evidence suggests that oxidative stress (see below) further aggravates vascular function in the placenta [Roberts, 1999], which in turn [Shennan et al., 2001] gives rise to impaired blood perfusion [Hung et al., 2002]. Vasoconstriction and elevated resistance to blood flow follow as a consequence. Our array results show involvement of genes in both redox regulation and inflammation [Hansson et al., 2005].

Stage 2. Decreased placental perfusion, in combination with oxidative stress, causes general endothelial cell damage within the placenta. In later part of stage 2, the endothelial inflammation also damage the maternal vascular system, the kidneys in particular, is a typical histological finding in PE [Roberts et al., 1989; de Groot and Taylor, 1993; Granger et al., 2001; Strevens et al, 2003]. The link between stage one and two has up to date not been known.

Generally, preeclampsia occurs in women during their first pregnancy, and more commonly affects teenagers and women over 35 years of age. Women with underlying diseases that predispose them to hypertension are also among those at greater risk for the development of this condition. Preeclampsia is a leading cause of maternal mortality and morbidity. It is accounting for 12-18% of all pregnancy-related maternal deaths (around 70 maternal deaths per year in the United States and an estimated 50,000 maternal deaths per year worldwide). It is also associated with a high perinatal mortality and morbidity, due primarily to iatrogenic prematurity. Neurological manifestations are common in preeclampsia, and include headaches, visual aberrations to more severe manifestations such as seizures, stroke, and cortical blindness. Delivery of the fetus and removal of the placenta is the only curative treatment for preeclampsia—a fact that has lead to the generally accepted theory that placental pathology is central to development of preeclampsia. Despite intensive research efforts, the aetiology of preeclampsia remains largely unknown.

As mentioned above, it is believed that inadequate placentation, resulting in reduced placental perfusion, is an early step in the development of PE. Reduced perfusion associated with increased vascular resistance can be detected with Doppler ultrasound, and women with evidence of increased resistance in the uterine arteries early in their pregnancies ("notching") have a higher risk of developing PE than women without this finding. As PE progresses, the maternal vascular bed is affected, and a general endothelial inflammation is seen. Poor placental perfusion appears to result in a cascade of pathological changes: decreased oxygen delivery, oxidative stress, formation of reactive oxygen species, endothelial damage, increased vascular permeability, and inflammation (see FIG. 1).

The symptoms of preeclampsia typically appear in the third trimester of pregnancy and are usually detected by routine monitoring of the woman's blood pressure and urine. However, these monitoring methods are ineffective for diagnosis of the syndrome at an early stage. Early diagnosis could reduce the risk to the subject or developing fetus and high risk patients could more specifically be monitored. Furthermore, effective treatment, that today still is lacking, would be ideal in combination with early detection.

Some methods of diagnosis have been described in the prior art but none of these have yet been successfully used in the clinic on a large scale. For example can be mentioned: U.S. Pat. No. 5,079,171 and U.S. Pat. No. 5,108,898, which disclose that preeclampsia, pregnancy-induced hypertension, and eclampsia can be diagnosed by identifying the presence of an endothelial cell marker, cellular fibronectin, in a sample of blood, plasma or serum of a pregnant woman, for example, by using a sandwich or competition immunoassay. The cellular fibronectin derives from endothelial cells that are ruptured or disturbed during the disease process. U.S. Pat. No. 5,238,819 discloses the diagnosis of preeclampsia using an assay to measure a mitogenic factor in blood. The mitogenic factor is a proteinaceous compound of about 160 kDa and is capable of stimulating fibroblast mitosis. Its presence is detected by detecting radiolabelled thymidine uptake by cells activated by the sera or plasma of a preeclamptic subject. This marker appears after damage to the maternal vascular bed already has occurred, hence late in the disease progression.

WO 05/093413 (Yale University and Brigham and Women's Hospital) discloses a method of diagnosing of severe preeclampsia in a pregnant woman, comprising measuring the level of free haemoglobin in a cerebrospinal fluid sample.

Currently, there are no known cures for preeclampsia. Preeclampsia can vary in severity from mild to life threatening. A mild form of preeclampsia can remain mild with bed rest and frequent monitoring. For moderate to severe cases, hospitalization is necessary and blood pressure medication and anticonvulsant medications to prevent seizures are prescribed. If the condition becomes life-threatening to the mother or the baby, the only cure is to terminate the pregnancy often resulting in a pre-term delivered baby.

Clearly, the lack of therapy for preeclampsia coupled with the age-old lack of ability to diagnose it until the the disease has progressed to a more severe form, prompts the need for novel approaches for diagnosing and treating preeclampsia, which is a significant public health problem.

DESCRIPTION OF THE INVENTION

Accordingly, there is a need for identifying biomarkers that reliably can identify i) pregnant subjects in risk of developing preeclampsia, ii) pregnant subjects suffering from early stage preeclampsia, and/or iii) pregnant subjects suffering from preeclampsia (irrespective of whether it has been diagnosed or not). Moreover, there is a need for developing treatment regimens for pregnant women in any of the groups i)-iii) mentioned above.

The present invention provides such a biomarker, namely fetal haemoglobin, which has been shown to enter the maternal circulatory system in pregnant women suffering from preeclampsia.

The present invention is based on the inventors' knowledge and realization that elevated levels of free fetal haemoglobin in a pregnant woman are associated with an increased risk to develop preeclampsia. Hence, free fetal haemoglobin can be used as a biomarker for the diagnosis of preeclampsia and it is also a candidate target for treatment of preeclampsia.

This biomarker enables detection of an increased risk to develop preeclampsia at an early stage, thus offering more hope of meaningful treatment. Also, the methods for diagnosis of preeclampsia according to the present invention can avoid unnecessary hospitalisation of pregnant women not being in the risk group. Furthermore, the method for monitoring the progression or regression of preeclampsia can help to plan the delivery of the fetus and decrease the risk for premature birth.

Preeclampsia has briefly been described herein before. In women, already after 12 gestational weeks, the utero-placental blood flow is established. The placenta barrier keeps the fetal blood circulation well separated from the maternal (see FIG. 2). The smallest functional units of the placenta, namely the villi, provide the foetus with nutrition and oxygen, transported over the barrier. In PE, however, decreased placental perfusion results in less oxygenated blood to the placenta. The lack of oxygen and uneven blood perfusion give rise to oxidative stress within the placenta. Oxidative stress induces apoptosis in the placental cells, which in turn causes inflammation and general endothelial cell damage within the placenta (see FIG. 3). When the placenta barrier is damaged, fetal cells can transfer into the maternal circulation. The knowledge of fetal cell transfer to the maternal circulation has been available for roughly ten years but no one has so far looked at free haemoglobin (i.e. haemoglobin found outside the cells (e.g. in plasma) and, accordingly, not bound in the cells. Mostly analysis of free fetal DNA has been examined.

Supported by the findings reported in the Experimental section herein, the present inventions have found elevated levels of free fetal haemoglobin (or of its subunits, the alpha and/or gamma chain) in patients suffering from PE. In women that do not suffer from PE, the level of free fetal haemoglobin should be around 0.038 μg/ml [Turpeinen et al, 1992] whereas our findings indicate a 20-fold increase to levels around 1 μg/ml, or more depending of the severity of the disease.

Even if there have been indications that women suffering from PE have increased level of total haemoglobin, no reports have until now shown that free fetal haemoglobin is a reliable indicator. Moreover, measurement of an incremental increase in the level of free fetal haemoglobin rather than an incremental increase in the total haemoglobin provides much more safe and reliable results. The reason is that the normal level of total haemoglobin is much higher than of fetal haemoglobin. If the level of fetal haemoglobin in plasma in a normal pregnant woman is 0.05 μg/ml and in a PE patient 1 μg/ml, then the increase is (1−0.05)/0.05×100=2000% (or 21-fold). In comparison, the levels of total haemoglobin in normal and PE patients are 3 μg/ml and 4.5 μg/ml, respectively (see example 5.1), which corresponds to an increase of (4.5−3)/3× 100=50% (or 1.5-fold).

As shown in FIG. 1, our results reported in the Examples herein indicate that fetal haemoglobin (Hb-F) is the link between stage 1 and stage 2. A placenta toxin has been a hypothesis for many years as indicator for PE. Stage I is known to take place in the placenta as a consequence of hypoxia due to altered perfusion. The placenta reaction then affects the maternal system but no specific factor has been identified. Based on the results presented in the Experimental section, the present inventors suggest that such a factor is fetal Hb according to the above mechanisms. Early diagnosis may help to follow women at risk of developing PE-"early health". Women with clinical signs of PE may be monitored as outpatient assuming that you can monitor the progression specifically, hence by following fetal Hb levels and/or fetal Hb/total Hb ratio. The need of a new treatment is obvious and the benefit of such would be tremendous.

The level of fetal haemoglobin may be used alone for the evaluation of whether a patient is in risk of or already has developed preeclampsia, but it may also be used in combination with the total level of haemoglobin or the level of adult haemoglobin present in the specific body sample as an indicator of disease progression.

In accordance with the present invention, it was surprisingly found that elevated levels of free haemoglobin, notably fetal haemoglobin, in a pregnant woman are associated with an increased risk to develop preeclampsia. Hence, fetal haemoglobin can be used as biomarker for the diagnosis of preeclampsia and it is also a candidate target for treatment of preeclampsia.

Based on this observation, the present invention relates to the following:
 i) a method for diagnosing PE
 ii) a method for evaluating progression or regression of PE
 iii) a method for assessing the effectiveness of a treatment of PE
 iv) a kit for use in one of the above-mentioned methods
 v) substances and compositions for use in the treatment of PE
 vi) human leukocyte antigen DPA1 (HLA-DPA1) as a biomarker Definitions In this specification, unless otherwise specified, "a" or "an" means "one or more".

As used in this specification, the term "preeclampsia" is defined in accordance with criteria established by the committee on Terminology of the American College of Obstetrics and Gynecology, that is, hypertension plus proteinuria, overt edema, or both. For example preeclampsia can be defined as blood pressure >140/90 mm Hg and proteinuria >0.3 g/L.

There exist different forms of haemoglobin. Adult haemoglobin (Haemoglobin A) consists of two alpha and two beta polypeptide chains (Hbα, Hbβ), each containing a non-peptide heme group that reversibly binds a single oxygen molecule. Haemoglobin A2, another adult haemoglobin component is composed of two alpha chains and two delta chains (Hbα, Hbδ). Fetal haemoglobin (Haemoglobin F) on the other hand is the major component of haemoglobin in the fetus. This haemoglobin has two alpha and two gamma polypeptide chains (Hbα, Hbγ).

The term "free haemoglobin", in this specification refers to free haemoglobin generally and includes total free haemoglobin, free haemoglobin A, free haemoglobin A2, free haemoglobin F, any free haemoglobin subunit (e.g. an Hbα, HIV, Hbβ or Hbγ chain), or any combination thereof. It further includes these haemoglobin entities in either a polypeptide (protein) or nucleotide (RNA) form, except when applied as a target for treatment. The term "free fetal haemoglobin" refers to free haemoglobin F or any subunit of haemoglobin F and includes the haemoglobin F entities in a polypeptide (protein) or nucleotide (RNA) form, except when applied as a target for treatment.

In this specification, the term "free" as used, inter alia, in the expressions "free haemoglobin", "free fetal haemoglobin" or "free haemoglobin subunits (e.g. Hbα, Hbβ, Hbδ or Hbγ chains)" refer to haemoglobin, fetal haemoglobin or haemoglobin subunits freely circulating in a biological fluid, as opposed to cellular haemoglobin which refers to the molecules residing inside cells. The term "free" in this sense is thus mainly used to distinguish free haemoglobin from haemoglobin which is present in intact erythrocytes.

The terms "marker" or "biomarker", in this specification, refer to a biomolecule, preferably, a polypeptide or protein, which is differentially present in a sample taken from a woman having preeclampsia or a woman at increased risk of developing preeclampsia as compared to a comparable sample taken from a woman, referred to as a "normal" woman/subject who does not have preeclampsia or is at increased risk of developing preeclampsia.

The term "biological sample from pregnant female mammal" or equivalents thereof is intended to denote a sample from the mammal itself; accordingly, the sample is not obtained from e.g. the foetus or the amniotic fluid.

Throughout the specification, any and all references are specifically incorporated into this patent application by reference.

Re i) Method for Diagnosing PE

According to a first aspect of the present invention, there is provided a method for the diagnosis or aiding in the diagnosis of preeclampsia comprising the following steps: (a) obtaining a biological sample from a pregnant female mammal; (b) measuring the level of free fetal haemoglobin or measuring the level of free fetal haemoglobin and the level of total free haemoglobin, in said biological sample; and (c) comparing the level of free fetal haemoglobin in the sample with a reference value or comparing the ratio between the level of free fetal haemoglobin and the level of total free haemoglobin in the sample with a reference value, to determine if said pregnant female has or has not preeclampsia, or is or is not at increased risk of developing preeclampsia.

The step of obtaining a biological sample from said pregnant female mammal includes the process of being provided with a biological sample obtained with standard methods well known in the art.

The biological sample could be, for example, blood, blood serum, plasma, urine, vaginal secretions, tears, tissue, serum, stool, sputum, amnion fluid and cerebrospinal fluid. In specific embodiments, the biological sample is blood, urine, amnion fluid or placental tissue.

In certain embodiments, the biological sample is blood, plasma, urine or placental tissue.

The sample size of the biological sample collected is varied according to individual needs and sensitivities. The amount collected can vary widely, depending on the type of testing being used, the site of collection, and the possibility of any adverse effects to the mother or fetus. In specific an embodiment, a blood sample size is somewhere in the range from about 5 to about 75 ml, preferably from about 20 to about 40 ml.

It is contemplated that the methods of this invention are applicable to any animal that is a "placental" animal, i.e., one that nurtures the unborn fetus through a placenta. Such animals include, among others, humans, other primates, mammalian food animals. A preferred animal for diagnosis is a human or a commercially valuable animal or livestock.

In a preferred embodiment, the mammal is a human.

In a certain embodiment, samples are collected from pregnant women. The pregnant woman may be an individual who has been determined to have a high risk of preeclampsia based on her personal or family history. Other; patients, inter alia, include pregnant women who are known to have preeclampsia and for whom the test is being used to determine the effectiveness of therapy or treatment they are receiving. Also, patients could include healthy pregnant women who are having a test as part of a routine examination.

If desired, the sample can be prepared to enhance detectability of free fetal haemoglobin. Typically, sample preparation involves fractionation of the sample and collection of fractions determined to contain free haemoglobin. Methods of pre-fractioning include, for example, centrifugation, RNA/DNA extraction, size exclusion chromatography, ion exchange chromatography, gel electrophoresis and liquid chromatography.

The step of measuring the level of free fetal haemoglobin can be accomplished by, for example, an immunological assay (e.g., an ELISA or other solid phase-based immunoassay such as SPRIA or amplified ELISA so called IMRAMP), a protein chip assay, quantitative real-time PCR amplification, surface-enhanced laser desorption/ionization (SELDI), high performance liquid chromatography, Mass Spectrometry, In situ hybridization, immunohistochemistry, chemiluninescence, nephelometry/turbometry, lateral flow or pure or polarised fluorescence or electrophoresis. However, it would be apparent to a person skilled in the art that this list of techniques is not complete and these techniques are not the only suitable methods which may be used in the present invention for measuring the level of free fetal haemoglobin.

The substances being detected and/or measured in the methods of the invention include total haemoglobin, haemoglobin A, haemoglobin A2, haemoglobin F, any of the haemoglobin chains (Hbα, Hbβ, Hbδ and Hbγ), or any combination thereof. In one specific embodiment of the invention, haemoglobin gamma chain (Hbγ) is detected and/or measured in the method of the invention. Clearly, haemoglobin F and its subunits are most important as the findings are based on increased levels of free fetal haemoglobin and its impact on the development of PE. As discussed herein, the gamma chain is indicative of fetal haemoglobin, whereas e.g. the beta and delta chain are indicative of adult haemoglobin. Based on the disclosure herein, a person skilled in the art will know which haemoglobin chain(s) that should be measured.

An immunological assay (immunoassay) can, according to the present invention, be used to measure the level of free haemoglobin. An immunoassay is an assay that uses an antibody to specifically bind an antigen (e.g., haemoglobin). The immunoassay is characterized by the use of specific binding properties of a particular antibody to isolate, target, and/or quantify the antigen. Thus, under designated immunoassay conditions, the specified antibodies bind to a particular protein at least two times the background and do not substantially bind in a significant amount to other proteins present in the sample. Using the purified markers or their nucleic acid sequences, antibodies that specifically bind to a marker (e.g., haemoglobin) can be prepared using any suitable methods known in the art [see e.g., Coligan, 1991].

In a certain embodiment of the first aspect, the free fetal haemoglobin level is measured e.g. using an immunological assay. Particularly, the immunological assay is an ELISA. However, as demonstrated in the Examples herein, Western Blotting may also be employed.

In a certain embodiment of the first aspect, the free fetal haemoglobin level is determined by measuring free fetal haemoglobin RNA. Particularly, free fetal haemoglobin RNA is measured using real-time PCR. In those cases where total haemoglobin level also is determined, this level may also be determined by measuring haemoglobin alpha-chain RNA, e.g. by using real-time PCR.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead.

After incubating the sample with antibodies, the mixture is washed and the antibody-marker complex formed can be detected. This can be accomplished by incubating the washed mixture with a detection reagent. This detection reagent may be, e.g., a second antibody which is labelled with a detectable label. Exemplary detectable labels include magnetic beads, fluorescent dyes, radiolabels, enzymes (e.g., horse radish peroxide, alkaline phosphatase and others commonly used in an ELISA), and calorimetric labels such as colloidal gold or coloured glass or plastic beads.

Alternatively, the marker in the sample can be detected using an indirect assay, wherein, for example, a second, labelled antibody is used to detect bound marker specific antibody, and/or in a competition or inhibition assay wherein, for example, a monoclonal antibody which binds to a distinct epitope of the marker is incubated simultaneously with the mixture.

Methods for measuring the amount or presence of an antibody-marker complex include, for example, detection of fluorescence, luminescence, chemiluminescence, absorbance, reflectance, transmittance, refractive index (e.g., surface plasmon resonance, ellipsometry, a resonant mirror method, a gating coupler waveguide method or interferometry) or radioactivity. Optical methods include microscopy (both confocal and non-confocal), imaging methods and non imaging methods. Electrochemical methods include voltametry and amperometry methods. Radio frequency methods include multipolar resonance spectroscopy.

Useful assays are well known in the art, including, for example, an enzyme immunoassay (EIA) such as enzyme-linked immunosorbent assay (ELISA), radioimmunoassays such as RIA and SPRIA; a Western blot assay; or a slot blot assay.

In a specific embodiment, an ELISA is the preferred method for measuring the level of free haemoglobin.

The step of measuring the level of free fetal haemoglobin, according to the present invention, can also be accomplished by detection and measurement of free RNA coding for haemoglobin polypeptides in the sample, e.g. detection of RNA sequences coding for haemoglobin gamma chain (Hbγ), or fragments thereof, in blood plasma.

According to a specific embodiment, free haemoglobin RNA is quantified using real-time PCR.

In the step of comparing the level of free haemoglobin in the sample with a reference value or comparing the ratio between the level of the free haemoglobin subunit and the level of total free haemoglobin in the sample with a reference value, the term "reference value" in relation to the present invention, according to an embodiment, refers to a determined baseline or mean level of free haemoglobin, i.e. the same sort of free haemoglobin being measured in step (b), or the ratio between the level of the free haemoglobin subunit and the level of total free haemoglobin, in samples from a control group. Preferably, the control group comprises pregnant female mammals not diagnosed with preeclampsia.

When using a control group, the determination of the reference value of free fetal haemoglobin is performed using standard methods of analysis well known in the art. The value will of course vary depending on, for example, the type of assay used, the form of free haemoglobin being measured, kind of biological sample, and group of subjects. For example, normal average blood levels of total free haemoglobin in a group of pregnant women not diagnosed with preeclampsia, and measured with an ELISA, are normally in the range of 2.5 to 3.5 µg/ml, but of course can vary depending on age, weight, number of earlier pregnancies etc.

In the case were said reference value is the level of free fetal haemoglobin or the ratio between the level of free fetal haemoglobin and the level of total free haemoglobin, in samples from a control group, a higher level of free fetal haemoglobin or a higher value of said ratio in the sample relative to the reference value indicates that said pregnant female has preeclampsia or is at increased risk of developing preeclampsia.

In a certain embodiment of the first aspect, the reference value is the level of free fetal haemoglobin or the ratio between the level of free fetal haemoglobin and the level of total free haemoglobin, in samples from a control group, wherein a higher level of free fetal haemoglobin or a higher value of said ratio in the sample relative to the reference value indicates that said pregnant female has preeclampsia or is at increased risk of developing preeclampsia. Preliminary results—using a Western Blot method for determination of free fetal haemoglobin—indicate that women having a plasma level of about 5 µg/ml or above or, alternatively a urine level of 1 µg/ml or above are subject to PE or to develop PE. These values, however, are expected to be better identified using a more sensitive method like e.g. ELISA. From the literature a normal plasma level of fetal haemoglobin of about 0.3-76 µg/l, i.e. 0.0003-0.076 µg/ml has been reported (see Turpeinen et al, 1992) with a mean value of 0.038 µg/ml. Accordingly, pronounced levels of fetal haemoglobin has been seen in women developing PE or already suffering from PE. Accordingly, it is contemplated that women having a plasma level of fetal haemoglobin 5-10 times or more above the normal level (i.e. 0.3 µg/ml or more) are at risk of developing PE. This value, however, is also expected to be better identified using a more sensitive method like e.g. ELISA. In specific embodiments, it is contemplated that if the plasma level of fetal haemoglobin is about 20 times or more, about 50 times or more, about 75 times or more or about 100 times or more then the woman is either at risk of developing PE or is suffering from PE either in stage 1 or 2. Viewed in another way and provided the above mentioned normal range applies, a woman is at risk or suffering from PE if the plasma level of free fetal haemoglobin is about 0.5 µg/ml or more such as, e.g., about 0.75 µg/ml or more, about 1 µg/ml or more, about 1.25 µg/ml or more, about 1.5 µg/ml or more, about 1.75 µg/ml or more, about 2 µg/ml or more, about 2.5 µg/ml or more, about 3 µg/ml or more, about 3.5 µg/ml or more, about 4 µg/ml or more, about 4.5 µg/ml or more, or about 5 µg/ml. It is contemplated that the lower the fetal haemoglobin level is the less severe is the disease at its present stage. The progression (or regression) of the disease can then be followed by frequent measurement of the fetal haemoglobin level of the same woman.

The results from the examples herein support the above considerations. Thus, using the Western blotting method about 20% of the women in group II (i.e. the group already suffering from PE) had a plasma level of 5 µg/ml or more. With respect to urine level about 20% of the women suffering from PE had a urine level of fetal Hb of 1 µg/ml or more (see Example 5.2). Accordingly, with respect to urine levels it seems as if the level is a bit lower than the plasma level and, accordingly, all the levels mentioned above for plasma apply, but the lower levels are reduced to about 0.06 µg/ml or more, about 0.1 µg/ml or more, about 0.2 µg/ml or more, 0.4 µg/ml or more etc, in urine.

Another way than looking at the exact plasma or urine level of fetal haemoglobin in order to judge whether a woman is at risk or already has indication of PE, is to look at the standard deviation for the test carried out when determining the plasma or urine level (or in fact the level in any other suitable body liquid). A relevant parameter is here contemplated to be an increase from the normal level (e.g. in plasma or urine etc.) with 5 times the standard deviation or more such as, e.g. 10 times the standard deviation or more, 25 times the standard deviation or more, 50 times the standard deviation or more or 100 times the standard deviation or more.

With respect to measurement of the ratio (R) between free fetal Hb (Hb F) and free total Hb (total Hb), the ratio of a normal woman (i.e. not suffering from PE) is about 0.038 µg/ml/3 µg/ml=0.012 when the two parameters are measured by time-resolved immunofluorimetric assay as described by Turpeinen et al., and ELISA as described below (Example 5). Accordingly, it is contemplated that a ratio R of 0.12 or more indicates that the woman is at risk or already has developed PE at a certain stage. In certain embodiments PE risk or disease at a certain stage is indicated if R is 0.15 or above such as, e.g., 0.2 or above, 0.3 or above, 0.4 or above, 0.5 or above or 0.6 or above. Theoretically, R=1 when all (100%) of free total Hb is fetal Hb. Hence, this is the upper limit.

The present invention also contemplates the use of the methods described herein in combination with other methods of diagnosis. Diagnostic methods that can be used in combination with the methods of the invention include current methods for diagnosing or aiding in the diagnosing of preeclampsia known to medical practitioners skilled in the art, as examples of such methods can be mentioned measuring the level of urate or the level of cystatin C in serum. A biological sample may first be analyzed by the methods described herein. The biological sample may then be tested by other methods to corroborate the observation. Hence, the accuracy of the diagnostic method of the present invention can be improved by combining it with other methods of diagnosis.

Re ii) Evaluation of Progression/Regression of PE

In further embodiments of the invention, free fetal haemoglobin, e.g. free fetal haemoglobin subunits, can be employed for determining preeclampsia status (e.g., severe preeclampsia) or for prognosis, i.e. prediction of the outcome of the disease, of the patient. For example, the concentration of free haemoglobin correlates with the severity of preeclampsia (e.g., mild or severe preeclampsia). It is known that neurological manifestations, such as seizures or coma (eclampsia), stroke, hypertensive encephalopathy, headaches, and visual aberrations (scotomata, diplopia, amaurosis, homonymous hemianopsia, are common in severe preeclampsia [Douglas and Redman, 1994].

Thus, according to the second aspect of the present invention, there is provided a method for monitoring the progression or regression of preeclampsia, comprising: (a) measuring the level of free fetal haemoglobin or measuring the level of free fetal haemoglobin and the level of total free haemoglobin, in a first biological sample isolated from a pregnant female mammal; (b) measuring the level of free fetal haemoglobin or measuring the level of free fetal haemoglobin and the level of total free haemoglobin, in a second biological sample isolated from said pregnant female mammal at a later time; and (c) comparing the values measured in step (a) and (b), wherein an increase in the free fetal haemoglobin level in the second sample relative to the free fetal haemoglobin level in the first sample or an increase in the ratio between the level of free fetal haemoglobin and the level of total free haemoglobin in the second sample relative to the ratio between the level of free fetal haemoglobin and the level of total free haemoglobin in the first sample, indicates preeclampsia progression; and a decrease in the free fetal haemoglobin level in the second sample relative to the free fetal haemoglobin level in the first sample or a decrease in the ratio between the level of free fetal haemoglobin and the level of total free haemoglobin in the second sample relative to the ratio between the level of free fetal haemoglobin and the level of total free haemoglobin in the first sample, indicates preeclampsia regression.

We conducted the field part of our study at Muhimbili Hospital in Dar es Salaam, Tanzania's major city (see Example 5). Muhimbili Hospital is a third level referral centre, receiving patients predominantly from the municipal hospitals. Muhimbili University of Health and Allied Sciences (MUHAS) is the only public university in the country offering higher education training in health sciences. The high numbers of pregnancies complicated by PE and eclamspia in Tanzania made it a suitable setting for our study. At Muhimbili Hospital, PE was found in 16% of the women attending the antenatal clinic. The hospital-based incidence of eclampsia was 200/10,000 deliveries based on a study during 1999-2000. This can be compared to the incidence of 5/10,000 maternities in Europe. Ten patients with severe PE or eclampsia and ten matched controls were included in the study (see the following table).

TABLE 1

Clinical characteristics at delivery of patients that participated in this study.

|  | PE | Control |
|---|---|---|
| Number[a] | 10 | 10 |
| Age (years) | 28.5 (19-40) | 21.5 (18-30) |
| Parity | 1.6 ± 2.3 | 0.6 ± 1.4 |
| Gestational age (days) | 256 (217-266) | 280 (231-287) |
| Systolic pressure (mmHg)*** | 191 ± 34 | 115 ± 9 |
| Diastolic pressure (mmHg)*** | 124 ± 18 | 74 ± 7 |
| Proteinuria (g/L)***,[b] | 2.6 ± 0.8 | 0.3 ± 1.0 |
| Birth weight (g) | 2005 ± 717 | 3040 ± 398 |
| Placenta weight (g) | 335 ± 120 | 506 ± 68 |
| Sectio (n) | 6 | 4 |
| IUFD (n) | 5 | 0 |
| Eclampsia (n) | 4 | 0 |

PE = Preeclampsia
One-way Anova with post-hoc Bonferroni test was used to statistically evaluate differences among the groups. A p-value < 0.05 was considered statistically significant.
***The test showed a significant difference between PE versus Control (p < 0.001).
[a]One case of maternal death within 24 hours after delivery in the PE group.
[b]Values for proteinuria are inexact due to method limitations. The highest measurable value was 3 g/l.

Patients were selected during a six-week period, September-October 2007, at the Department of Gynaecology and Obstetrics at Muhimbili Hospital. The preeclamptic group was selected from the eclamptic intensive care ward, where an average of two PE patients per day was admitted. The inclusion criterias were either severe PE (diastolic blood pressure ≥110 mmHg on two occasions) or eclampsia. All patients with documented chronic hypertension before pregnancy were excluded from the study. The patients were interviewed using a question sheet translated to Swahili. Hospital charts for each participating patient were studied in order to get additional information. Women included in the study had persistent elevation of blood pressure during the initial 24 hours of hospitalization and a proteinuria ≥1 g/l. Age, parity, number of antenatal visits, mode of delivery, admission to delivery interval, maternal and fetal outcomes were noted.

Urine samples collected before delivery showed a statistically significant difference in total haemoglobin levels between the PE and control groups (FIG. 21). Statistical calculations were made by a non-parametric Mann-Whitney U-test, which showed a p-value of 0.0093. The median value for the preeclamptic group was 31.0 µg/ml compared to 2.5 µg/ml in the control group. The high value of the control group is most likely due to high incidence of malaria. Urine samples collected after delivery were also analysed.

In specific embodiments it is contemplated that an increase in free fetal haemoglobin level corresponding to two standard deviations or more such as, e.g., 3 or more, 4 or more, 5 or more, 7 or more or 10 or more standard deviations is indicative of an increased risk for developing PE and/or progression of the disease. In an analogous matter a decrease in free fetal haemoglobin level corresponding to two standard deviations or more such as, e.g., 3 or more, 4 or more, 5 or more, 7 or more or 10 or more standard deviations is indicative of an decreased risk for developing PE and/or regression of the disease. Another measure can be the ratio ($R_t$) between the Hb F at time $t_2$ and Hb F at time $t_1$ where $t_1$ is the time for the first sample was taken and $t_2$ is the time the second sample was taken. An increase in $R_t$ is indicative of a progression of the disease and a decrease in $R_t$ is indicative of a regression of the disease. As the individual variation is expected to be minimal due to the fact that it is the same woman that is subject for testing, it is believed than even a small increase or decrease is a valid indicator. A value of $R_t$ of 1.1 or more is expected to be indicative of a progression of the disease, whereas a value of $R_t$ of 0.9 or less is indicative of a regression of the disease.

In those cases, where the ratio R (i.e. the ratio between Hb F and total Hb) is employed the measure is typically the ratio between R ($R_2$) obtained at a second point in time and R obtained at a first point in time ($R_1$). An increase in $R_2/R_1$ is indicative of a progression of the disease and a decrease in $R_2/R_1$ is indicative of a regression of the disease. As the individual variation is expected to be minimal due to the fact that it is the same woman that is subject for testing, it is believed than even a small increase or decrease is a valid indicator. A value of the ratio $R_2/R_1$ of 1.1 or more is expected to be indicative of a progression of the disease, whereas a value of the ratio $R_2/R_1$ of 0.9 or less is indicative of a regression of the disease.

The details mentioned under the first aspect also apply to this and the following aspects.

Re iii) A Method for Assessing the Effectiveness of a Specific Treatment of PE

According to the third aspect of the present invention, there is provided a method of assessing the efficacy of a treatment for preeclampsia comprising the following steps: (a) measuring the level of free fetal haemoglobin or measuring the level of free fetal haemoglobin and the level of total free haemoglobin, in a first biological sample obtained from a pregnant female mammal before treatment; (b) measuring the level of free fetal haemoglobin or measuring the level of free fetal haemoglobin and the level of total free haemoglobin, in a second biological sample from the same pregnant mammal after treatment; and (c) comparing the level or the levels determined in (a) with the level or the levels determined in (b), wherein a decrease in the free fetal haemoglobin level in the second sample relative to the free fetal haemoglobin level in the first sample or a decrease in the ratio between the level of free fetal haemoglobin and the level of total free haemoglobin in the second sample relative to the ratio between the level of free fetal haemoglobin and the level of total free haemoglobin in the first sample, indicates that the treatment is efficacious for treating preeclampsia.

In specific embodiments it is contemplated that the efficacy of the treatment can be evaluated by determining any decrease in free fetal haemoglobin level. If the decrease corresponds to two standard deviations or more such as, e.g., 3 or more, 4 or more, 5 or more, 7 or more or 10 or more standard deviations it is indicative of the treatment being effective in reducing the progression of PE and/or treating the disease and/or alleviating the symptoms associated with the disease. In an analogous matter an increase in free fetal haemoglobin level corresponding to two standard deviations or more such as, e.g., 3 or more, 4 or more, 5 or more, 7 or more or 10 or more standard deviations is indicative of an ineffective treatment Another measure can be the ratio ($R_t$) between the Hb F at time $t_2$ and Hb F at time $t_1$ where $t_1$ is the time for the first sample was taken and $t_2$ is the time the second sample was taken. An increase in $R_t$ is indicative of a progression of the disease, i.e. the treatment is not sufficient, whereas a decrease in $R_t$ is indicative of a regression of the disease and an effective treatment. As the individual variation is expected to be minimal due to the fact that it is the same woman that is subject for testing, it is believed than even a small increase or decrease is a valid indicator. A value of $R_t$ of 1.1 or more is expected to be indicative of a progression of the disease, whereas a value of $R_t$ of 0.9 or less is indicative of a regression of the disease.

In those cases, where the ratio R (i.e. the ratio between Hb F and total Hb) is employed the measure is typically the ratio between R ($R_2$) obtained at a second point in time and R obtained at a first point in time ($R_1$). An increase in $R_2/R_1$ is indicative of a progression of the disease, i.e. the treatment does not seem to be sufficient, and a decrease in $R_2/R_1$ is indicative of a regression of the disease, i.e. the treatment seems to have the desired effect. As the individual variation is expected to be minimal due to the fact that it is the same woman that is subject for testing, it is believed than even a small increase or decrease is a valid indicator. A value of the ratio $R_2/R_1$ of 1.1 or more is expected to be indicative of a progression of the disease, whereas a value of the ratio $R_2/R_1$ of 0.9 or less is indicative of a regression of the disease.

Re iv) Diagnostic Kit

According to the fourth aspect of the present invention, there is provided an assay kit for the diagnosis or aiding in the diagnosis of preeclampsia, according to the present invention, comprising means for measuring the level of free fetal haemoglobin in a biological sample of a pregnant female mammal and instructions for using said detecting means.

The present invention provides kits for diagnosis or aiding in the diagnosis of preeclampsia. The kits are used to detect or screen for the presence of free haemoglobin that are differentially present in samples from subjects with preeclampsia.

In one embodiment, the kit comprises means for detecting in a biological sample of a pregnant female mammal levels of free haemoglobin (e.g. haemoglobin alpha chain (Hbα), haemoglobin beta chain (Hbβ), haemoglobin delta chain (Hbδ), haemoglobin gamma chain (Hbγ) and total free haemoglobin), either singly or in combination with other detecting means and instructions for using said detecting means. Alternatively or additionally, a kit according to the invention comprises means for measuring fetal Hb mRNA.

In a preferred embodiment, the kit comprises means for detecting the level of free fetal haemoglobin, e.g. means for measuring the level of haemoglobin gamma chain (Hbγ) in a sample. In another embodiment, it further comprises means for detecting the level of total free haemoglobin.

In one embodiment, the means for detecting comprises antibodies specific for haemoglobin, preferably for fetal haemoglobin (e.g. an anti-human-Hbγ antibody).

In a further embodiment, said instructions comprise suitable operational parameters in the form of a label or separate insert. For example, the instructions may inform a consumer how to collect the sample and how to wash the probe. Especially care should be taken to minimize haemolysis of blood samples to avoid false values of total Hb.

A kit to be used in the method of the invention can further comprise analyte standards, reagents etc.

In a certain embodiment of the fourth aspect, the level of free fetal haemoglobin is determined by measuring the level of haemoglobin gamma chain (Hbγ).

In a certain embodiment of the fourth aspect, the assay kit further comprises means for detecting the level of total free haemoglobin e.g. to determine ratios of total Hb versus fetal Hb and/or versus fetal Hb mRNA.

More specifically, a diagnosis kit of the invention can for example comprise all components (except water) that are needed to perform an ELISA designed to measure the fetal haemoglobin-concentration in a sample or two ELISAs designed to measure both the fetal haemoglobin- and total haemoglobin-concentrations in a sample. A preferred way to measure the concentrations of fetal haemoglobin is the competetive variant of ELISA described here below:

Haemoglobin-F, diluted to 1-5 µg/ml in a water solution, is coated to 96-well microtiter plates by incubation overnight. Pre-coated plates will be provided ready for use in the kit. The microtiter plate wells should be incubated at the clinic with a mixture, containing 50 µl rabbit anti-haemoglobin-F, diluted 1000-10000 times with water solution A (for example 0.9% NaCl containing 0.1% of a detergent, for example Tween 20, and 0.1% of bovine serum albumin), plus either 50 µl of a series of standard oxyhaemoglobin-F samples, diluted with water solution A to the concentrations 1-10000 ng/ml, or 50 µl of the patient samples (diluted 100-10000× with water solution A). This mixture should be left in the microtiter plate wells for a time-period between 30 minutes and 3 hours at room temperature. The plates should then be washed 3 times with water solution A, and each well incubated for 30 minutes with 100 µl swine-anti-rabbit IgG-alkaline phosphatase (ALP), diluted 1000-10000× in water solution A. The plates should then be washed 3 times with water solution A and finally incubated with a substrate that ALP can react specifically with, turning it into a coloured product. The substrate solution can be, for example, 1 mg/ml p-nitrophenyl phosphate in 1M diethanolamine+0.5 mM $MgCl_2$, pH 9.8. The concentration of the product (=colour intensity) in a well is then proportional to the amount of anti haemoglobin-F in that well, and the amount of antibody is, in turn, reversely proportional to the amount of haemoglobin-F in the patient or control sample. The colour intensity can be determined exactly by a light absorbance-type microtiter plate-reader, or even estimated by the eye.

The enzyme horse-radish peroxidase (HRP), rather than ALP, is the obvious choice of enzyme couple to the secondary antibodies for a person skilled in the art. In this context, however, HRP cannot be used because haemoglobin, which will be present in the same microtiter plate wells, is also an peroxidase enzyme and will give falsely high values of the coloured product.

To our knowledge, a competetive ELISA using a polyclonal rabbit antiserum in combination with ALP has not previously been used to measure fetal haemoglobin-F.

A manual, containing instructions concerning procedure, exact volumes, dilutions, concentrations, incubation times and temperatures of each step and reagent, will be provided with the kit. Also provided are precoated microtiter plates, solutions of oxyhaemoglobin-F or "total" oxyhaemoglobin for coating and a standard dilution series, a solution of rabbit anti-haemoglobin-F or rabbit anti-total haemoglobin, a solution of swine anti-rabbit IgG-ALP, a solution of ALP-substrate and water solution A.

Oxyhaemoglobin-F and "total" oxyhaemoglobin will be prepared at our laboratories as follows. Red blood cells from 50 ml human chord blood (preparation of Hb-F) or adult blood (preparation of total Hb) are isolated by centrifugation (1200×g, 10 minutes) and washed 4 times with 10 volumes of phosphate buffered saline (PBS, 10 mM phosphate, pH 7.4; 120 mM NaCl and 3 mM KCl). The blood cells are then lysed by resuspension in hypotonic buffer (20 volumes $H_2O$:1 volume PBS) on ice. The membranes are separated from the cytosol by centrifugation (14000×g, 20 minutes) and the supernatant dialysed 3 times against 15 mM Tris-HCl, pH 8.0 in 4° C. Two-hundred ml of DEAE-Sepharose (GE Healthcare) is packed in a column and the dialysed supernatant applied to the gel and separated by a gradient consisting of 15 mM Tris-HCl, pH 8.0 and 15 mM Tris-HCl, pH 8.0+0.2 M NaCl. Fractions are collected and the absorbance measured at 280 nm, 577 nm and 630 nm to identify and determine the concentration of oxyhemoglobin-F or total oxyhaemoglobin [Winterbourn, 1990]. The solution for coating and the standard series are prepared by dilution in water solution A.

Rabbit anti-total haemoglobin is bought from Dako, Denmark and rabbit anti-haemoglobin-F is prepared by immunization of rabbits with purified haemoglobin γ-chain (Hb-γ) and bleeding the rabbits according to standard protocols. The immunization and bleeding is done at a commercial institute ("outsourcing"). Hb-γ is purified from Hb-F at our laboratory by dissociating and separating the α- and γ-chains, mainly following the protocols of Kajita et al. [1969] and Noble [1971]. Potassium-fosfate (0.1 ml 1M $KH_2PO_4$) and sodium chloride (0.2 ml 2M NaCl) are added to 10 ml of a 3% (w/v) solution of haemoglobin-F. Fifty mg of p-mercuribenzoate are dissolved in 0.2 ml 1M NaOH and 1 ml water added to this. These two solutions are mixed, carefully titrated with 1M acetic acid to pH 4.5 and left overnight gently moving in the cold. The next morning, pH is adjusted to 7 with 1M NaOH and centrifuged (5000×g, 10 minutes, 10° C.). The pellet is discarded and the supernatant is dialyzed against 10 mM Tris-HCl, pH 7.5. The dialyzed sample is then applied to a 10-ml DEAE-Sepharose (GE Healthcare) column, which had been pre-equilibrated with 10 mM Tris-HCl, pH 7.5. After the sample application, the column is rinsed with 50 ml 10 mM Tris-HCl, pH 7.5 and then with a salt-buffer gradient consisting of 100 ml 10 mM Tris-HCl, pH 7.5 and 100 ml 10 mM Tris-HCl, pH 7.5+0.2 M NaCl. Sample application, washing and gradient elution is done at a flow of 40 ml/hour and collecting 3-ml fractions. The α- and γ-chain concentrations of each eluted fraction are then evaluated by light absorbance at 415 nm, SDS-PAGE, native PAGE and aminoterminal amino acid sequencing. Fractions containing pure γ-chain are pooled, 2-mercaptoethanol added up to 50 mM to dissociate the p-mercuribenzoate from the half-cystines. The p-mercuribenzoate is then removed from the protein by desalting on a Sephadex G-25 column (PD-10, GE Healthcare), eluting with 0.1M sodium fosfate, pH 7.5+50 mM 2-mercaptoethanol. Finally, the eluted protein fractions dialyzed against 0.1M sodium fosfate, pH 7.5.

Swine anti-rabbit IgG-ALP is bought from Sigma, whereas the substrate solution and water solution A are prepared at our laboratory from commercially available chemicals.

Alternatively, the fetal haemoglobin-ELISA may be a sandwich-type of ELISA using a monoclonal or polyclonal antibody specific for Hb-γ for coating, the clinical sample at an appropriate dilution or a standard fetal haemoglobin series in incubation step 1 and a rabbit anti-haemoglobin-ALP in the second incubation step.

Alternatively, a protein chip coated with a monoclonal antibody specifically reacting with Hb-γ may be used in the diagnosis kit as a means of measuring the concentration of fetal haemoglobin in the clinical samples.

Re v) Substances and Compositions for Use in the Prevention and/or Treatment of PE In accordance with the findings reported herein that free fetal haemoglobin is an indicator of PE and that a reduction in the Hb F level (or Hb level in general) is likely to reduce any progression of the disease, it is contemplated that any substance that has i) the ability to inhibit formation of free Hb (free Hb F or any other Hb), ii) the ability to bind free Hb (free Hb F or any other Hb), or iii) the ability to reduce the concentration of circulating free Hb (free Hb F or any other Hb) would be a potential substance for effective treatment and/or prevention of PE. Accordingly, in a further aspect of the present invention, there is provided a use of at least one member selected from the group consisting of haemoglobin binding agents; heme binding/degradation agents; iron-binding agents; agents that stimulate haemoglobin degradation, heme degradation and/or iron sequestering; and/or agents that inhibit placental hematopoiesis for the treatment of PE. Moreover, in a further aspect of the present invention, there is provided the use of such a substance for the manufacture of a pharmaceutical preparation for the treatment or prophylaxis of preeclampsia.

The terms "treatment or prophylaxis" in their various grammatical forms in relation to the present invention refer to preventing, curing, reversing, attenuating, alleviating, ameliorating, inhibiting, minimizing, suppressing, or halting (1) the deleterious effects of preeclampsia, (2) disorder progression, or (3) disorder causative agent.

Haemoglobin is critical to oxygenation, but free haemoglobin in the circulation is toxic to tissues by altering the vascular redox balance during the auto-oxidation of heme from its ferrous to ferric state [Motterlini et al., 1995] and possibly through the induction of globin-centered free radicals [Svistunenko et al., 1997].

Applicants propose that increased levels of free haemoglobin in the blood of women with preeclampsia not only serves as a marker for the disease, but is also responsible, or partly responsible, for the disease manifestations commonly seen in such patients. Hence, free haemoglobin is also a candidate target for treatment of preeclampsia. Even if free fetal haemoglobin is regarded as a marker for PE it is contemplated that reduction of free haemoglobin in general (i.e. fetal haemoglobin as well as more unspecific haemoglobin such as, e.g., adult haemoglobin) will minimize the progress of or treat PE.

In a certain embodiment of this aspect, the haemoglobin binding agents and/or heme binding agent is alpha 1-microglobulin. Henceforth, this agent will be called alpha-1-microglobulin or $\alpha_1$-microglobulin and abbreviated $\alpha_1$m. Other names for this substance that have been used in the scientific literature are protein HC (heterogeneous in charge; human complex-forming), AMBP-protein and alpha-1-microglycoprotein but these names are synonymous to $\alpha_1$m.

In a certain embodiment of this aspect, the haemoglobin binding agents and/or heme binding agent is an antibody specific for haemoglobin and/or heme.

Accordingly, the present invention also provides a method for the treatment or prophylaxis of preeclampsia, which method comprises administering to a subject in need for such treatment or prophylaxis of an effective amount of one or more of such agents mentioned above including at least one member selected from the group consisting of haemoglobin binding agents and/or heme binding/degradation agents and/or iron-binding agents; agents that stimulate haemoglobin degradation and/or heme degradation and/or iron sequestering; and agents that inhibit placental hematopoiesis. The agent may typically be administered in the form of a pharmaceutical composition comprising the active agent in combination with one or more pharmaceutically acceptable excipients.

Moreover, the present invention provides the use of at least one member selected from the group consisting of haemoglobin binding agents and/or heme binding/degradation agents, agents that stimulate haemoglobin degradation and/or heme degradation and/or iron sequestering, and agents that inhibit placental hematopoiesis for the manufacture of a pharmaceutical preparation for the treatment or prophylaxis of preeclampsia; and a method for the treatment or prophylaxis of preeclampsia, which method comprises administering to a subject in need for such treatment or prophylaxis of an effective amount of a pharmaceutical preparation comprising at least one member selected from the group consisting of haemoglobin binding agents and/or heme binding/degradation agents and/or iron sequestering agents, agents that stimulate haemoglobin degradation and/or heme degradation and/or iron sequestering, and agents that inhibit placental hematopoiesis. In these aspects the aim is to decrease the amount of free haemoglobin and its degradation product heme, in for example maternal blood, to prevent tissue damage and further progress of the disease.

The haemoglobin binding agents and/or heme binding/degradation agents are compounds, which exhibit haemoglobin and/or heme binding/degradation properties. The iron sequestering agents are compounds which bind free iron and prevent it from participating in the redox reactions.

In one embodiment, the haemoglobin binding agents and/or heme binding/degradation agent is $\alpha_1$m. This small plasma and tissue protein is a heme-binder [Allhorn et al., 2002; Larsson et al., 2004] and radical scavenger [Åkerström et al. 2007] and a heme-degrading form, t-$\alpha_1$m, is induced by proteolytic removal of a C-terminal tetrapeptide, LIPR when $\alpha_1$m is mixed with free haemoglobin [Allhorn et al., 2002]. It can also bind to haemoglobin in placentas (see below). Free haemoglobin and reactive oxygen species causes an increased production of $\alpha_1$m in liver cells and blood cells [Olsson et al. 2007]. Therefore, $\alpha_1$m is a potential heme- and haemoglobin antagonist that can protect against heme- and haemoglobin-induced damage to cells and tissue components. Examples 5.4-5.7 provide further evidence to this. Thus, example 5.4 shows that preeclamptic patients respond to the disease by increasing the levels of $\alpha_1$m, example 5.5 shows that $\alpha_1$m inhibits and repairs heme-induced oxidative damage on cells and tissues, example 5.6 describes an in vitro model of placenta where tests of therapy-agents can be taken one step closer to in vivo tests, and example 5.7 shows that haemoglobin is bound by $\alpha_1$m in placenta-tissue.

Other agents that are contemplated to be potential active agents for the treatment or prevention of PE are the following:

Haemoglobin-Binders:

Antibodies

Monoclonal antibodies with strong binding of haemoglobin and blocking of redox enzyme activity of haemoglobin can be developed. The antibodies can be produced by in vivo or in vitro immunization or selected from pre-existing libraries. The antibodies may be selected for specificity against alpha-, beta- delta- or gamma-globin chains, or against common parts of these globin chains. The antibodies can be modified to make them suitable for therapy in humans, i.e. provided with a human immunoglobulin framework. Any part of antibodies may be used: Fv-, Fab-fragments or whole immunoglobulin.

Haptoglobulin

Haptoglobulin is a glycoprotein found in blood plasma. Three forms of haptoglobin exist, Hp1-1, Hp2-1 and Hp2-2. All forms bind to haemoglobin and forms a Hp-Hb complex. The Hb-Hp complex has weaker redox enzymatic activity than free haemoglobin and does therefore cause less oxidative damage. Binding to Hb prevents, for example, iron loss from the heme group.

CD163

CD163 is a scavenger receptor, found on macrophages, monocytes and reticuloendothelial system lining the blood vessels. The receptor recognizes the Hp-Hb complex and mediates endocytosis and delivery of this to the lysosomes, degradation by HO-1 (see below) and sequestration of free iron by cellular ferritin. CD163 therefore contributes to the elimination of haemoglobin-induced oxidative stress.

Heme-Binders/Degraders:

Hemopexin

Hemopexin is a glycoprotein (60 kDa) found in human blood plasma, and which eliminates free heme from blood plasma by binding it strongly (Kd appr 1 pmol/L) and transporting the heme to the liver for degradation in the reticuloendothelial system.

Heme-Oxygenase

Heme-oxygenase is a cellular heme-binding and degradation enzyme complex that converts heme to biliverdin, carbon monoxide and free iron. The latter is sequestered by cellular ferritin and biliverdin is reduced by biliverdin reductase to bilirubin which is ultimately excreted into the urine. Three forms of heme oxygenase genes, with very different structures, have been described, HO-1, HO-2 and HO-3. HO-1 is the most important. This gene is upregulated in virtually all cells in the body by haemoglobin, free heme, hypoxia, free radicals, ROS (reactive oxygen species) and many different inflammatory signals. HO-1 is a strong anti-oxidant because it eliminates the oxidants heme and iron, but also because it produces bilirubin, which has anti-oxidant effects against some oxidants.

Albumin

Albumin is a 66 kDa protein in human blood plasma that can bind heme. There is no evidence of cellular uptake and degradation of the albumin-heme complex, and the effect of albumin is probably to act as a depot of heme thus preventing heme from entering endothelial cell membranes, vessel basal membranes, etc.

Iron-Binders:

Transferrin

Transferrin is the most important transporter of iron in blood. The transferrin-iron complex is recognized and bound by cellular receptors which internalize and dissociate the complex.

Ferritin

This multimeric protein, consisting of 24 subunits of two types, is the major intracellular depot of free iron. It has a high iron-storing capacity, 4500 iron atoms/ferritin molecule. Bound to ferritin, iron is largely prevented from oxidation and reduction reactions, and hence from causing oxidative damage.

In a further embodiment, the haemoglobin binding agent is an antibody specific for haemoglobin and/or heme.

In specific embodiments, the pharmaceutical preparation comprises a combination of haemoglobin binding agents and/or heme binding agents and/or iron sequestering agents.

Agents that stimulate haemoglobin degradation and/or heme degradation include, but are not limited to, proteins like haptoglobin, hemopexin and heme oxygenase.

The pharmaceutical preparations of the present invention may be administered to a "placental" animal, such as a human, other primate, or mammalian food animal. A preferred animal for administration is a human or a commercially valuable animal or livestock.

Administration may be performed in different ways depending on what animal to treat, on the condition of the animal in the need of said treatment, and the specific indication to treat. The route of administration may be oral, rectal, parenteral, or through a nasogastric tube. Examples of parenteral routes of administration are intravenous, intraperitoneal, intramuscular, or subcutaneous injection.

Formulation of the pharmaceutical preparation must be selected depending not only on pharmacological properties of the active ingredient but also on its physicochemical properties and the kind administration route. Different methods of formulating pharmaceutical preparations are well known to those skilled in the art.

For parenteral compositions, liquid compositions are preferred or solid compositions designed to be reconstituted with e.g. an aqueous medium before application. Suitable excipients include: solvents (e.g. water, aqueous medium, alcohols, vegetable oils, lipids, organic solvents like propylene glycol and the like), osmotic pressure adjusters (e.g. sodium chloride, mannitol and the like), solubilizers, pH adjusting agents, preservatives (if relevant), absorption enhancers etc.

For oral compositions, the compositions may be in solid, semi-solid or liquid form. Suitable compositions include solid dosage forms (e.g. tablets including all kinds of tablets, sachets, and capsules), powders, granules, pellets, beads, syrups, mixtures, suspensions, emulsions and the like.

Suitable excipients include e.g. fillers, binders, disintegrants, lubricating agents etc. (for solid dosage forms or compositions in solid form), solvents such as, e.g., water, organic solvents, vegetable oils etc. for liquid or semi-solid forms. Moreover, additives like pH adjusting agents, taste-masking agents, flavours, stabilising agents etc. may be added.

Moreover, specific carriers to target the active substance to a specific part of the body can be included. For example an antibody-$\alpha_1$m complex where the antibody is targeted to placenta ("homing") by its specificity for a placenta-epitope; a stem cell or a recombinant cell with placenta-homing properties, e.g. integrin-receptors specific for placenta and with the artificial or natural capacity to secrete large amounts of $\alpha_1$m. The treatment would be more efficient since the drug would be concentrated to placenta.

The term "effective amount" in relation to the present invention refers to that amount which provides a therapeutic effect for a given condition and administration regimen. This is a predetermined quantity of active material calculated to produce a desired therapeutic effect in association with the required additives and diluents; i.e., a carrier, or administration vehicle. Further, it is intended to mean an amount sufficient to reduce and most preferably prevent a clinically significant deficit in the activity and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents; i.e., carrier, or additive. Further, the dosage to be administered will vary depending on the active principle or principles to be used, the age, weight etc of the patient to be treated but will generally be within the range from 0.001 to 1000 mg/kg body weight/day. Moreover, the dose depends on the administration route.

Re vi) HLA-DPA-1 as a Biomarker

A further aspect of the invention relates to the observation that fetal cells can trigger the maternal immune response since they are different. The role of the HLA gene family is to present foreign antigen to the maternal immune system. Women that express the HLA-DPA1 gene may "see" the fetal cells on an early stage, which could help protecting them from further damage. (In the studies reported herein, we have observed that women with notch, but not developing PE, expressed HLA-DPA1.)

Accordingly, HLA-DPA1 can be used as an indirect indicator for fetal haemoglobin and/or for PE. Thus, in a further aspect of the present invention, there is provided a method of prognosis for preeclampsia comprising the following steps: (a) obtaining a biological sample from a pregnant female mammal; (b) measuring the level of human leukocyte antigen DPA1 (HLA-DPA1), in said biological sample; and (c) comparing the level of HLA-DPA1 in the sample with a reference value. It is contemplated that if the above-mentioned HLA compositions are present, the female is probably at less risk to develop PE (with or without free fetal HB), whereas if the female does not have this protective HLA, then she is at higher risk, especially if also free fetal Hb level increases.

In a certain embodiment of this aspect, the steps (a) to (c) are performed to determine if said pregnant female is or is not at increased risk of developing preeclampsia or is or is not at increased risk of developing a severe form of preeclampsia.

In a certain embodiment of this aspect, an expression or a high expression of HLA-DPA1 indicates a better prognosis than no expression of HLA-DPA1.

In a last aspect of the present invention, there is provided a assay kit for the prognosis or aiding in the prognosis of preeclampsia, according to the method of prognosis for preeclampsia according to the invention, comprising means for detecting, in a biological sample of a pregnant female mammal, levels of HLA-DPA1 and instructions for using said detecting means.

The present invention will now be described in more detail.

Figure 1:
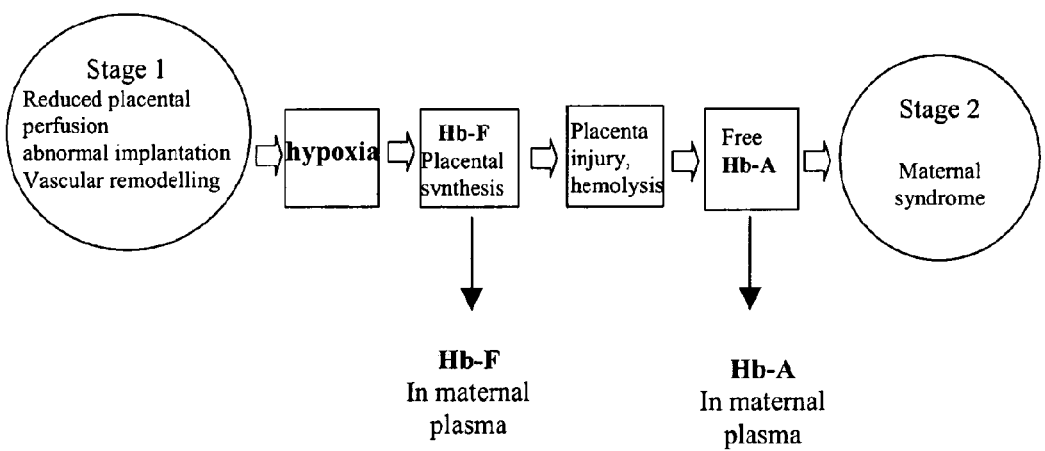
FIG. 1 shows an extended model of preeclampsia development, based on the findings of Hb-F and Hb-A in maternal blood plasma, high-lighting the appearance of Hb-F and Hb-A and their possible use as markers of different stages of the disease.
Figure 2:
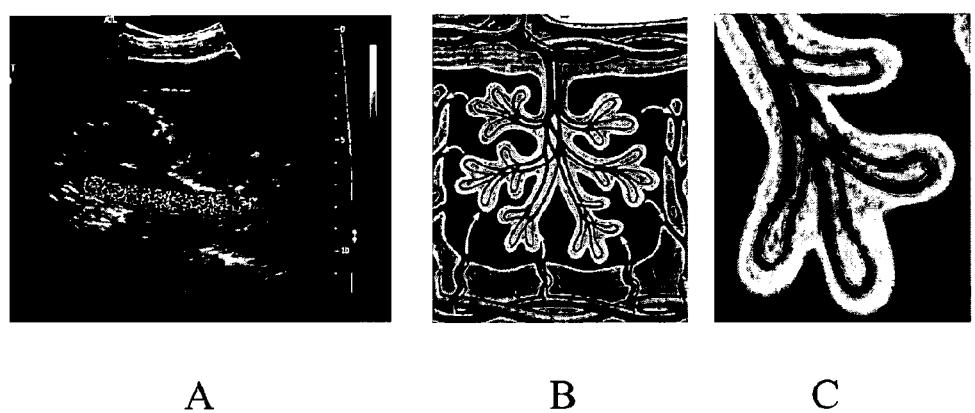
FIG. 2A shows the placenta in early pregnancy (ultrasound), B shows the fetal circulation in the villi, dipping down in the intervillous space filled with maternal blood and C shows the smallest functional unit-villi with the fetal circulation.
Figure 3:
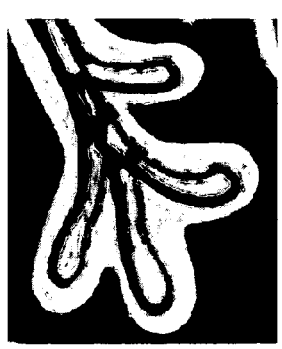
FIG. 3A shows the fetal circulation in the villi, dipping down in the intervillous space filled with less oxygenated maternal blood (darker), B shows that apoptosis (oval dots) is induced in the placental cells-trophoblasts, by reactive oxidative species (ROS), and C shows the blood-placenta barrier is damaged.
Figure 3:
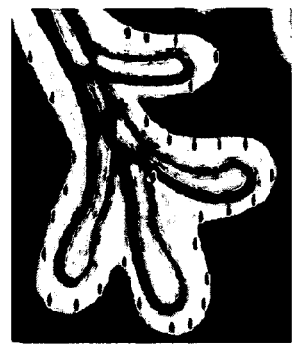
Figure 3:
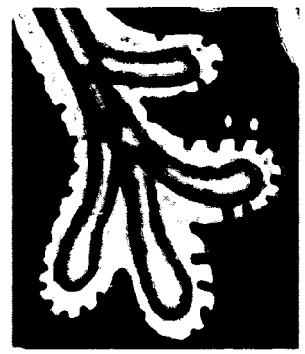

The following examples are given to illustrate the present invention. It should be understood, however, that the invention is not intended to be limited to the specific conditions and details described in these examples.

EXAMPLE 1

Detection of Hb RNA and Protein in Placenta

Quantitative RT-PCR, In situ hybridization and immunohistochemistry was performed to analyze Hbα, Hbβ and Hbγ mRNA and protein expression in placental samples in PE vs. control subjects.

Sample Collection

Placental tissue was collected at the Department of Obstetrics and Gynaecology, Lund University Hospital. The sampling, performed with written consent, was approved by the Ethical Committee Review Board for studies in human subjects. Placental tissue from 10 preeclamptic, 15 normal pregnancies, 5 patients with bilateral notch and 5 patients with bilateral notch as well as preeclampsia were included in the study. Placental bed samples (see below) from 5 of the patients with PE and 5 of the controls were also collected. Preeclampsia was defined as blood pressure >140/90 mm Hg and proteinuria >0.3 g/L. Patients with essential hypertension or other systemic diseases were excluded. Placenta samples were collected at birth, immediately frozen and stored at −80° C.

Tissue Sampling and Handling

Placental samples were collected immediately after delivery. A 10×10×10 mm cube of villous tissue was removed from the central part of the placenta avoiding macroscopic areas of necrosis and infarction. 10×10×10 mm cubes of myometrial tissue were collected from women undergoing caesarian section. The samples were immediately frozen on dry ice, and stored at −80° C. until RNA was extracted. The tissue was not thawed prior to RNA extraction or cryosectioning to ensure the highest possible RNA integrity.

RNA Extraction

Total RNA was extracted from frozen tissue using Trizol® (Invitrogen) according to the manufacturer's instructions. Proteoglycan and polysaccharide were removed by performing a high-salt precipitation with 0.8 M sodium citrate and 1.2 M sodium chloride.

RNA integrity was determined by denaturing 1% agarose gel electrophoresis with 6.7% formalin and 1× MOPS buffer. Samples were stored in RNAse free water at −80° C. until usage. Prior to usage samples were once more precipitated and washed with 70% ethanol to remove Trizol residues.

Real-Time PCR Amplification cDNA was synthesized with reverse transcriptase according to protocols from Applied Biosystems. A 50 μl reaction containing 0.5 μg total RNA, 1× Taq Man RT buffer, 5.5 mM MgCl2, 500 μM dNTPs, 2.5 μM random hexamers, 0.4 U/μl RNase inhibitor and 1.25 U/μl MultiScribe Reverse Transcriptase was used. The reactions were incubated at 25° C. for 10 minutes, at 48° C. for 30 minutes and finally 5 minutes at 95° C. Samples were stored at −20° C. until analysis.

Gene transcripts were assayed by means of real-time PCR using an ABI PRISM® 7000 sequence detection system (Applied Biosystems). Primers and probes were designed using the Primer Express® software program or ordered from Assays on-Design/Demand™ (Applied Biosystems). The primers targeted different exons of the genes of interest to avoid amplifying contaminating genomic DNA. Reactions were carried out in a 25 μl final volume containing: 1× Universal PCR Master Mix (Applied Biosystems), 0.25 μmol/l probe, 0.9 μmol/l of forward and reverse primers respectively, and 1 μl of 10 ng/μl of a DNA aliquot. The thermal cycling conditions were initiated by UNG activation at 50° C. for 2 minutes and an initial denaturation at 95° C. for 10 minutes. Then 40 cycles were run: 95° C. for 15 seconds, 60° C. for 1 minute. Two negative controls with no template were included in every set of amplifications. β-actin was used as a reference to normalize the signal from the sample. Quantisation was achieved by making a calibration curve using serial 4-fold dilutions of the template DNA (0.08-80 ng). Results are expressed as ratios with β-actin as the denominator.

In Situ Hybridization (ISHH)

The hybridizations were conducted as previously described in [Hansson et al., 2005]. Cryostat sections were thaw mounted onto sialinized slides, which were stored at −80° C. until they were used. Fresh frozen tissue was employed to maximize mRNA detection. Sections were fixed, dehydrated, dilipidated, and hybridized as previously described [Bradley et al., 1992]. Hybridizations were carried out for 20-24 hours in 55° C. with 2×106 cpm of denatured 35S-cRNA probe per 80 μl hybridization buffer (20 mM Tris-HCl (pH 7.4), 1 mM EDTA (pH 8.0), 300 mM NaCl, 50% formamide, 10% dextran sulphate, 1×Denhardt's 25 mg/ml yeast tRNA, 100 μg/ml salmon sperm DNA, 250 μg/ml total yeast RNA (fraction XI, Sigma), 150 mM dithiothreitol (DTT), 0.15% sodium thiosulfate (NTS) and 0.15% sodium dodecyl sulphate (SDS). Following washes, slides were apposed to Kodak Hyperfilm Biomax MR for 2 days, after which they were coated with nuclear track emulsion (NTB-3, Kodak). Slides were exposed for 3 (Hbα2, Hbγ2) respectively 4 (Hbβ) weeks at 4° C., after which they were developed in Dektol (Kodak), fixed and counterstained with a Giemsa stain.

Immunohistochemistry

14 µm thick fresh frozen sections of the placenta samples were fixed by immersion in 4% buffered formaldehyde for 10 min at room temperature. Sections were then incubated in a blocking solution (Powerblock; Zymed) for 30 minutes at RT. After PBS washes the sections were transferred into a 1:500 dilution of an anti-human fetal Hb antibody (Bethyl Laboratories) that was raised in sheep. Following an hour RT incubation the sections were rinsed and transferred into a 1:1000 dilution of an anti-sheep CY3 antibody raised in donkey (Jackson laboratories) for an hour at RT. The sections were then rinsed, coverslipped with 0.1M Tris and viewed under a Leica DMA 6000 inverted fluorescent microscope. Pictures were taken using Volocity software.

Results

Figure 4:
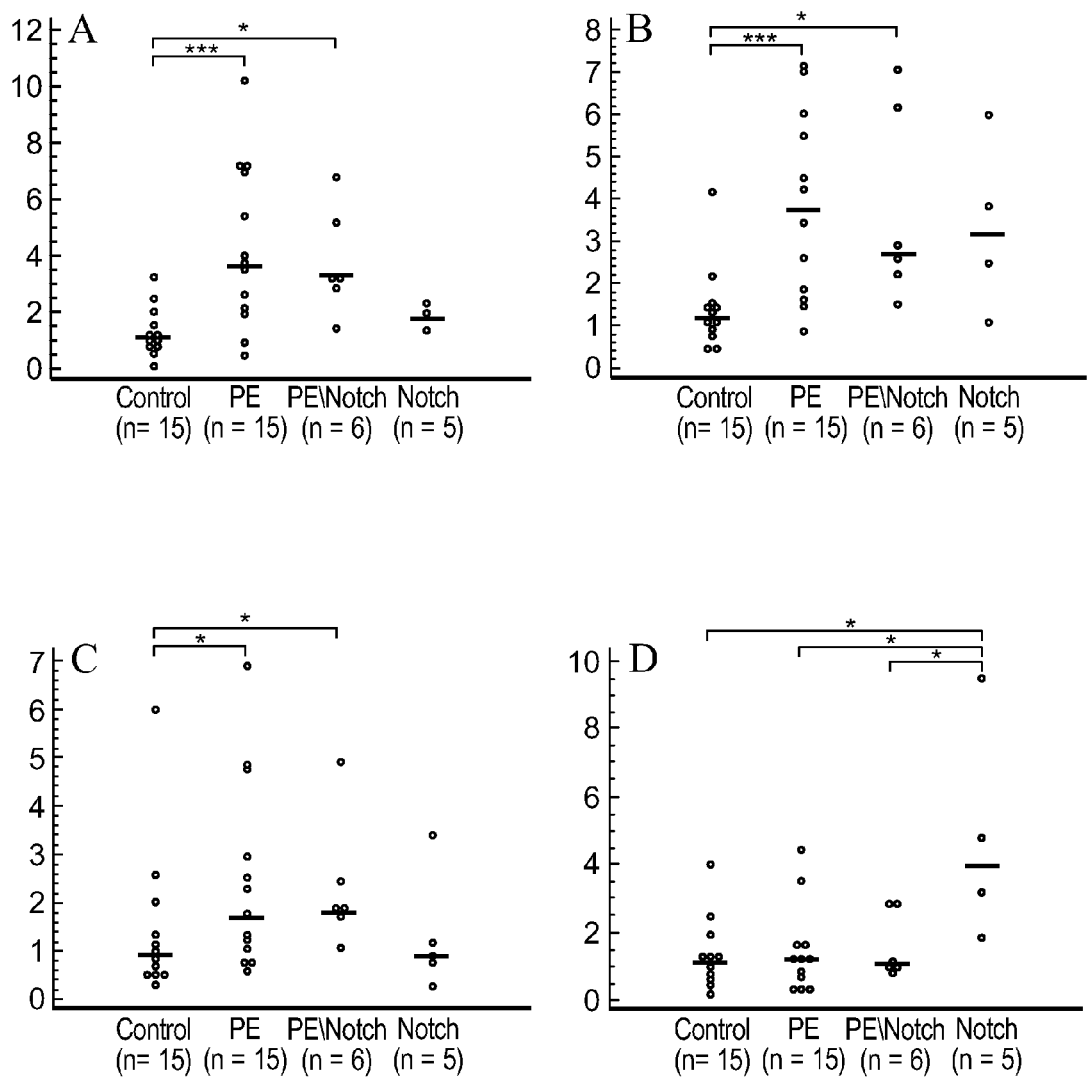
FIG. 4 (A-D) shows results from real-time PCR quantification of Hbα, Hbγ, Hbβ, and HLA-DPA1 mRNA in placenta.

FIG. 4 shows Real-time PCR quantification of Hbα, Hbγ and Hbβ in placenta. All values are normalized against the amount of β-actin and presented as scatter plots. (A) Hbα mRNA expression in the placenta. Significant changes were found between PE vs. controls (p=0.004) and between PE\Notch (PE with notching) vs. controls (p=0.03). (B) Hbγ relative mRNA values showing significant changes between PE vs. controls (p=0.003) and between PE\Notch vs. controls (p=0.03). (C) Hbβ showed significant overexpression in PE vs. controls (p=0.02) and in PE\Notch vs. controls (p=0.04).

To summarise, the levels of Hbα (p=0.004), Hbγ (p=0.003) and Hbβ (p=0.02) mRNAs were found to be significantly increased in PE samples vs. controls (FIG. 4A, B, C) and also in samples from PE with notching compared to controls (Hbα p=0.02, Hbγ p=0.03 and Hbβ p=0.04). (Hbβ was not represented on the array, but was examined because of changes detected in Hbα and Hbγ.)

Figure 5:
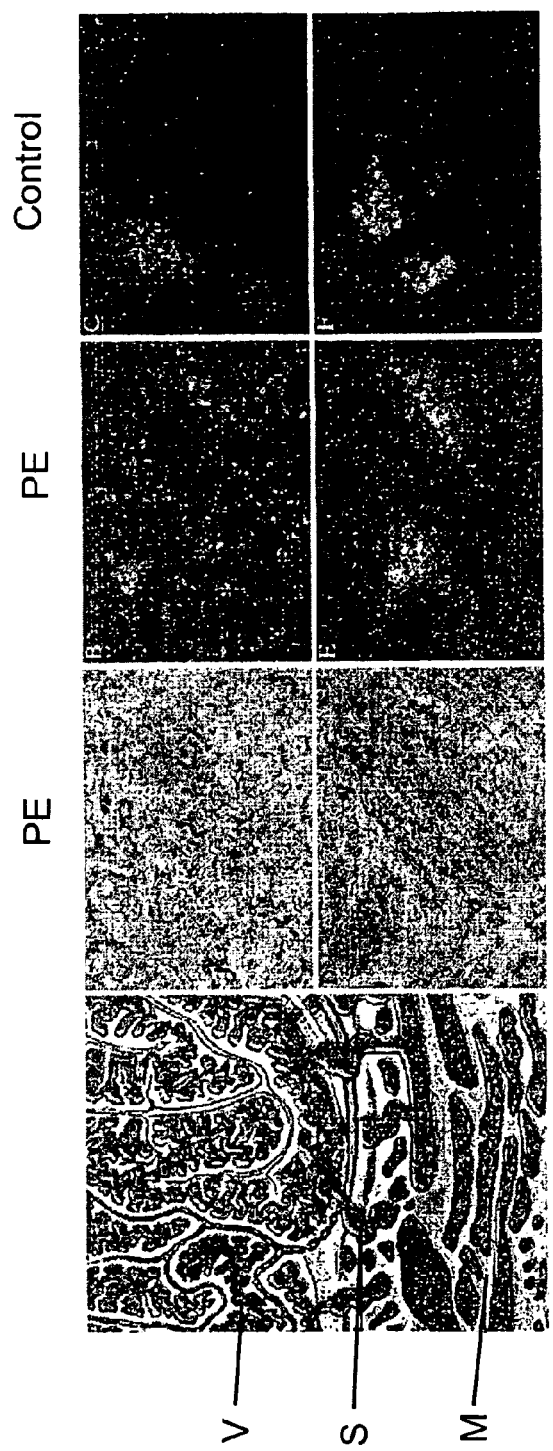
FIG. 5 shows images of in situ hybridizations from human placenta and placenta bed samples.

FIG. 5 shows results from in situ hybridizations from placenta and placenta bed samples. It shows images of the human placenta showing the villous section (V) of the placenta and below a placenta bed section (M) with spiral arteries (S) in between. (A) A light field image of Hbα mRNA-expression in a representative preeclamptic placenta sample. Hbα expression was especially seen in and around blood vessels. However, several scattered cells in the inter-villous space are also seen. (B) Darkfield image of the same section. (C) A darkfield image of Hbα mRNA expression from a representative control placenta. Compared with PE placentas, the control placentas show fewer Hbα-expressing cells in the inter-villous space. (D) Light field image from a representative myometrial sample from a PE patient. Hbα expression is only seen in the spiral arteries, no expression is seen in the myometrial tissue. (E) The same myometrial section in dark field. (F) A myometrial sample from a control placenta. Hbα mRNA expression is similar to the expression seen in PE myometrium.

To summarise, in situ hybridization revealed nucleated Hbα- and Hbγ-expressing cells which were scattered throughout the inter-villous space in both PE and control samples. Placentas from PE patients seemed to have more Hb containing cells than control samples (fetabl Hb), and the signals per cell appeared to be more intense than in controls. In several of the samples studied, Hb-positive cells were associated with the walls of blood vessels, with several cells free in the lumen. Many single cells were found in the intra-villous space. Based on their morphology, location, and distribution, they are not trophoblasts.

Figure 6:
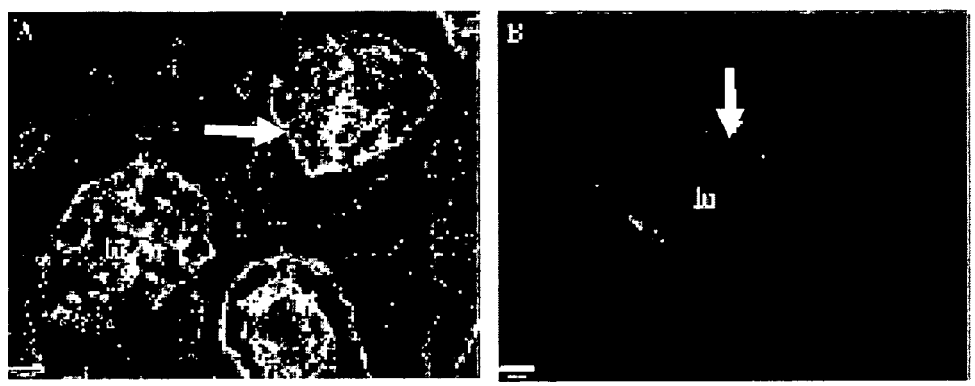
FIG. 6 is a representative image of Hbγ protein expression in the placenta.

FIG. 6. is a representative image of Hbγ protein expression in the placenta. Protein expression is shown with a red fluorescent marker. In the PE placenta there is a strong expression of Hbγ in the vascular lumen (lu), but Hbγ is also expressed in the vascular endothelium (arrow) (A). The placenta from normotensive controls however, showed no expression of Hbγ in the vascular lumen (B) but Hbγ (i.e. free fetal haemoglobin) is expressed in the vascular endothelium (arrow). The scale bars in the images are 25 µm.

To summarise, Hbγ-expression was especially detected within placental blood vessel lumen in PE placenta samples but also near the endothelial cells in the vascular walls. The control placenta samples showed Hbγ-expression in the vascular endothelium, with no expression in the vascular lumen.

Discussion

Quantitative RT-PCR showed an increased expression of Hbα and Hbγ mRNA in PE vs. controls. In situ hybridization showed an increased number of cells expressing Hb in placental samples from PE vs. control subjects. The fact that Hb expressing cells were located in association with vessel walls, may either indicate that the cells are migrating into or out of the vessels, or that there are binding sites on vessel walls for these cells. The fact that myometrial vessels are poor in nucleated cells that express Hb mRNAs vs. placental vessels, which are rich in them suggests that these cells may not be of maternal origin. Our finding that (fetal) Hbγ mRNA is present in the placental Hb-positive cells, as well as the lower number of cells expressing Hb in the myometrial blood vessel lumen, indicate that it is fetal cells that are responsible for the increased Hb expression seen in PE placentas and in blood.

If the fetal Hb-producing cells that we have described turn over quickly, they might release high levels of heme into the extra-villous space and the placental blood vessels. Indeed, our immunohistochemistry shows high levels of haemoglobin in the PE placenta blood vessel lumen. The control placenta on the other hand showed no release of haemoglobin into the blood vessels. To make matters worse, haemolysis in necrotic and thrombotic areas of the PE placenta may add to the amount of free heme there.

Free heme is a potent redox agent which can cause severe damage through the creation of reactive oxygen species (ROS). Heme oxidizes several lipids including low-density lipoproteins (LDL), converting them into cytotoxic peroxides which cause endothelial damage. Furthermore, heme can directly damage cell membranes by disrupting them and oxidizing membrane proteins leading to increased membrane permeability and cytolysis.

Thus, infiltration of the placenta by large numbers of Hb positive cells (i.e. fetal cells) is a worrisome sign. Heme released from these cells could be quite harmful and may be responsible for much of the placental pathology associated with PE.

In conclusion, without wanting to be bound to a theory, it is believed that our findings suggest that Hb genes are over expressed in a subpopulation of cells in the preeclamptic placenta. The production of agents that stimulate hematopoiesis by placental cells in response to reduced perfusion and possibly local hypoxia may contribute to the formation, recruitment and distribution of the cells. While they seem to be present in the placenta of subjects who had normal pregnancies, their increase in the placenta from PE patients is a matter of concern. If they turn over rapidly and release their Hb (and heme) excessively, they may damage adjacent structures including the vascular endothelium.

EXAMPLE 2

Detection of Fetal Hb in Maternal Blood

Quantitative RT-PCR was performed to analyze Hbγ mRNA in blood samples in PE subjects.

Real-Time PCR

RNA was extracted using QIAamp Viral RNA mini kit (Qiagen) according to manufacturer's instructions. Briefly, 3.6 ml of AVL Buffer was mixed with 36 μl of carrier-RNA (Qiagen) by inverting the tube 10 times. 1 ml of the plasma sample was spun at 1150 g for 10 minutes. 900 μl of the plasma and 3.6 μl of 99% ethanol was added to the AVL buffer solution. Approximately 650 μl of the solution was added to a QIAamp column and spun at 6000 g for 1 minute. This was repeated until the total plasma volume had been added to the column. Column was washed once with AW1 buffer, then spun at 6000 g for 1 minute, followed by a wash with AW2 buffer, then spun at 20,000 g for 3 minutes. RNA was eluated with 50 μl RNAse free water.

Fetal Hb RNA was quantified with real-time PCR.

Results

Figure 7:
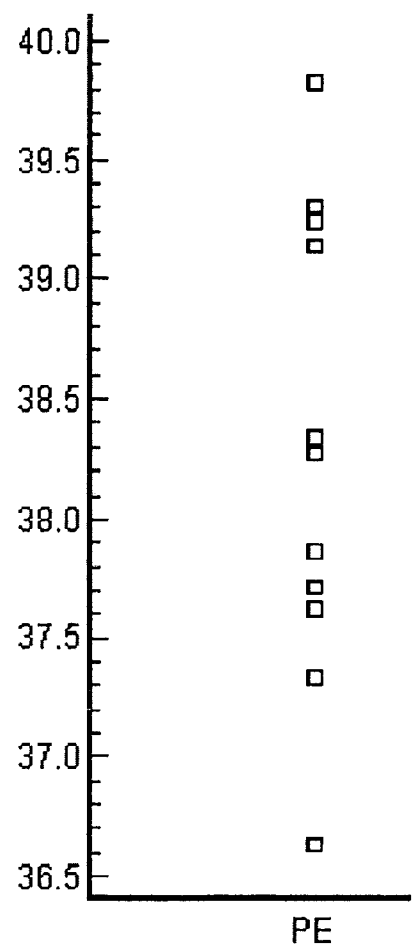
FIG. 7 shows a scatter plot of Hbγ mRNA levels in maternal plasma taken before delivery from women with PE quantified by real-time PCR. The plot shows the Ct value on the left axis, giving an estimate of the quantity of Hbγ mRNA levels in the sample.

FIG. 7 shows a scatter plot of fetal Hbγ mRNA levels in maternal plasma taken before delivery from women with PE quantified by real-time PCR. The plot shows the Ct value on the left axis, giving an estimate of the quantity of Hbγ mRNA levels in the sample. This shows that it is not only possible to measure protein levels of haemoglobin γ in maternal blood samples, but also mRNA quantities.

EXAMPLE 3

Protein Expression Profiling of the Preeclamptic Placenta Using 2D-Gel Electrophoresis In order to screen for differentially expressed proteins in the PE placenta compared to control placentas, we collected placenta samples at delivery from women with PE (n=30) and healthy controls (n=30). Using proteomics technology (2-dimensional gel electrophoresis) we compared haemoglobin delta (Hbδ) expression levels in the different placenta samples.

Patients and Sample Collection 60 women admitted at the Department of Obstetrics and Gynaecology, Lund University Hospital were included, and assigned to two groups; PE (n=30) and control (n=30) (Table 2). PE was defined as blood pressure of >140/90 mmHg and proteinuria of >0.3 g/l or rise in blood pressure above 20 mmHg from the first trimester of pregnancy. A 10×10×10 mm cube of placenta tissue was collected immediately after removal of the placenta. Samples were immediately frozen on dry ice and stored at −80° C. Patients with other systemic diseases were excluded from the study. The study was approved by the Ethical Committee Review Board for studies in human subjects, and all women gave their written informed consents.

TABLE 2

|  | Control | PE |
|---|---|---|
| n | 30 | 30 ns |
| Maternal age (years) | 31.7 ± 5.2 | 30.9 ± 5.3 ns |
| Gestational age (days) | 271.3 ± 10.8 | 266.6 ± 11.2 ns |
| Systolic pressure (mmHg) | 116.3 ± 11.3 | 149.8 ± 12.1† |
| Diastolic pressure (mmHg) | 67.3 ± 4.4 | 103.3 ± 7.9† |
| Proteinuria (g/L) | ND | 1.4 ± 2.0† |
| Placental weight (g) | 686.8 ± 144.8 | 630.9 ± 128.0 ns |

PE = Preeclampsia
ND = Not detected
ns—no significant difference between groups
†Mann-Whitney test showed a significance of $p < 0.0001$ between the groups Protein Extraction Protein was extracted using Trizol® (Invitrogen) according to manufacturer's instructions. Briefly, placenta tissue was homogenized in Trizol on ice and was then centrifuged at 12000 g for 10 min at 4° C. The protein fraction was separated using chloroform and precipitated using 2-propanol. The protein pellet was washed three times in 1.5 ml 0.3M guanidine hydro-chloride and once in 1.5 ml 75% ethanol. Pellets were dissolved 0.8 M urea and 2% chaps and protein concentration was measured using spectrophotometric procedure. Proteins were stored in −20° C. until usage.

Protein Precipitation

Prior to isoelectric focusing (IEF), samples were precipitated with acetone to inactivate proteolytic enzymes, remove salt and interfering substances. Extracted protein from each placenta, 400 μg, was mixed with ice-cold acetone to final concentration of 80% acetone. Samples were incubated for 1 h at −20° C. followed by centrifugation at 9000×g for 2 min. The acetone was removed and the protein pellets were allowed to air dry.

Two-dimensional Gel Electrophoresis

Immobiline Dry strips (180×3×0.5 mm, pH 3-10 NL, GE Healthcare Life Sciences) were rehydrated in 350 μl of the solubilisation solution containing 8 M urea, 2% CHAPS, 10 mM dithiothreitol (DTT) and 2% IPG 3-10 buffer together with 400 or 800 μg samples in room temperature over night. The IEF step was performed at 20° C. using a Multiphor II and run according to the following schedule: (1) 150 V for 1 h, (2) 300 V for 3 h, and (3) 3000 V until approximately 60 000 vhrs were reached. The strips were equilibrated for 10 min in a solution containing 65 mM DTT, 6 M urea, 30% (w/v) glycerol, 2% (w/v) sodium dodecyl sulphate (SDS) and 50 mM Tris-HCl pH 8.8. A second equilibration step was also carried out for 10 min in the same solution except for DTT, which was replaced by 259 mM iodoacetamide. The strips were soaked in electrophoresis buffer (24 mM Tris base, 0.2 M glycine and 0.1% SDS) just before the second dimension. The strips were applied on 12.5% homogeneous Duracryl slabgel (240×190×1 mm, or 290×245×1 mm). The strips were overlaid with a solution of 1% agarose in electrophoresis buffer (kept at 60° C.). Electrophoresis were carried either using a Hoefer DALT gel apparatus (Amersham Pharmacia Biotech, San Francisco, Calif., USA) at 20° C. and constant 80 V for 19 hrs or using a gel apparatus using the same electrophoresis buffer as above and run at 20° C. at 18 mA until the dye front reaches the bottom of the gel. The running time was about 17 hrs.

Gel Staining

Gels were silver stained, and after staining the gels were dried using a gel dryer (Slab gel Dryer SGD2000, Savant)

Spot Analysis

Gels were scanned using a CanoScan 995OF (Canon). Spot analysis was performed using PDQUEST (version 7.1.0) two-dimensional gel analysis system (Bio-Rad discovery series, Bio-Rad Laboratories, Sundbyberg, Sweden).

Mass Spectrometry Identification

The spots of interest were washed with 0.5 ml Milli-Q water for 1 h followed by four washes of 0.5 ml 40% acetonitrile (ACN) in 25 mM ammonium bicarbonate for 30 minutes each. Gel pieces were then dried in a SpeedVac concentrator before proteins were degraded into characteristic fragments with trypsin (sequencing grade, Promega) in 25 mM ammonium bicarbonate over night at 37° C. Digestion was terminated by addition of 20 µl 2% trifluoro acetic acid, which also extracted the peptides from the gel. After 2 hours at room temperature the peptides were purified from the digestion buffer using C18 Ziptips (Millipore). Briefly, the solid phase was conditioned using 2×10 µl 50% ACN, 0.1% TFA in Milli-Q water. The organic solvent was washed away by two washes of 10 µl 0.1% TFA. The samples were aspirated and dispensed several times followed by two washes of 0.1% TFA to remove salts and unbound material. The purified peptides were eluted directly onto the sample target (Anchorchip target, Bruker Daltonik) where 0.7 µl of matrix, 2,5-dihydroxybenzoic acid (3 mg/ml in 30% ACN) had been added. Mass spectra of positively charged ions were recorded on a Bruker Reflex III instrument (Bruker Daltonik) operated in the reflector mode. A total of 160-210 single shot spectra were accumulated from each sample. The XMASS 5.0 and MS Biotools software packages provided by the manufactures were used for data processing. Known auto proteolysis products from the trypsin were used for internal calibration.

MS/MS Analysis

From each of the peptide extracts, 0.5 µl was spotted directly onto a stainless steel MALDI target and was left to dry. 0.5 µl of a matrix solution containing 5 mg/ml α-cyano-4-hydroxy cinnamic acid, 50% acetonitrile, 0.1% TFA and 50 mM citric acid was added and allowed to dry. MALDI-TOF-MS and MS/MS spectra were acquired using a 4700 Proteomics Analyzer (Applied Biosystems, Framingham, Calif., USA) mass spectrometer in positive reflector mode. The obtained MS spectra were internally calibrated using two trypsin autoproteolysis peptides with the m/z values 842.51 and 2211.097. Protein identification was performed using the GPS Explorer software, with an in-house Mascot search engine (Matrix Science, London, UK) {Perkins, 1999 #132} searching the NCBI non-redundant database. Parameters specified in the search were: taxa, Mammalia; missed cleavages, 1; peptide mass tolerance, +/−30 ppm; fragment ion mass tolerance, +/−0.15 Da; variable modifications, none.

Database Searching

For protein identification, human protein sequences in the NCBI database were searched using the ProFound Peptide Mapping (version 4.10.5, The Rockefeller University Edition) and Mascot Software (Matrix Science Ltd).

Western Blot

Western blot was run on 12% Bis-Tris gels (Invitrogen, USA) according to manufacturer's instruction. Briefly, 20 µg protein with 2.5 ml LDS sample buffer (Invitrogen, USA) was loaded onto the gel and run for 50 min at 200V in 1× MOPS running buffer. Following electrophoresis the gel was blotted onto a PDVF membrane (Bio-Rad, USA) for 1 h at 30V, after which the membrane was incubated with Tris Buffered Saline (TBS) containing 0.1% Tween20® (ICN Biomedichals Inc., Ohio, USA) and 2% dry milk (Bio-Rad, USA) over night in 4° C.

The blot was incubated with primary mouse monoclonal IgG1 antibody (anti-human-Hbγ (diluted 1:8000 in TBS-T with 2% dry milk) (Nordic Biosite AB, Sweden) for 1 h, after which the membrane was washed once for 15 min in TBS-T and 3×5 min in TBS-T. Following washes, blot was incubated with goat anti-mouse IgG1-HRP secondary antibody (diluted 1:5000 in TBS-T) (SDS Santa Cruz Biotechnology, USA) for 1 h, after which the membrane was washed as above. Subsequently, the membrane was exposed to Enhanced chemilumeniscence ECL+(GE Healthcare Biosciences, UK) for 3 min. Autoradiographic film (Hyperfilm ECL, Amersham, USA) was applied to the blot for 1 minute to obtain satisfactory exposure.

RNA Extraction

Total RNA was extracted according to manufacturer's instruction using RNEasy (Qiagen) from 10 PE-samples and 10 control-samples from the same patients as above. Briefly, placenta samples were homogenized using TissueLyzer in an RNEeasy lysis buffer (RLTbuffert and β-mercaptoethanol) (Qiagen). Samples were precipitated in 70% ethanol and then separated using RNEasy mini columns according to manufacturer's protocol. Samples were eluted in 50 µl RNAse-free H2O.

Real Time PCR (same as Above)

cDNA was synthesized using reverse transcriptase according to the manufacturer's protocol (Applied Biosystems). Briefly, a 50 µl reaction mix (0.5 µg total RNA, 1× TaqMan RT buffer, 5.5 mM MgCl2, 500 µM dNTPs, 2.5 µM random hexamers, 0.4 U/µl RNase inhibitor and 1.25 U/µl MultiScribe Reverse Transcriptase) was used. The reactions were incubated at 25° C. (10 min), at 48° C. (30 min) and finally at 95° C. (5 min). Samples were stored at −20° C. until analysis.

Acquired gene transcripts were quantified by means of quantitative RT-PCR using an ABI PRISM® 7000 sequence detection system (Applied Biosystems). Primers and probes for TF (assay ID: Hs00169070_m1) and Hbδ (assay ID: Hs00426283_m1) were ordered from Assays-on-Demand™ (Applied Biosystems). The primers covered at least one exon boundary to avoid amplification of contaminating genomic DNA. Reactions were carried out in a 25 µl final volume containing final concentrations: 1× Universal PCR Master Mix (Applied Biosystems), 0.25 µmol/l probe, 0.9 µmol/l of forward and reverse primers respectively, and 2.2 µl of DNA aliquot. Thermal cycling was initiated by UNG activation at 50° C. for 2 minutes and an initial denaturation at 95° C. for 10 minutes. Following denaturation, 40 cycles were run: 95° C. for 15 seconds, 60° C. for 1 minute. Two negative controls, containing no template, were included in every set of amplifications. β-actin was used as a reference to normalize the signal from the sample. Quantification was achieved by making a calibration curve using serial 4-fold dilutions of the template DNA (0.08-80 ng). Results are expressed as ratios with β-actin as the denominator.

In Situ Hybridization (Same as Above)

In situ hybridization was conducted on 18 PE samples and 19 control samples. Cryostat sections were thaw mounted onto sialinized slides, which were stored at −80° C. until usage. Fresh frozen tissue was used in order to maximize mRNA detection. Sections were fixed, dehydrated, dilipidated, and hybridized. Hybridization was carried out for 20-24 hours in 55° C. with 2×106 cpm of denatured 35S-cRNA probe per 80 µl hybridization buffer (20 mM Tris-HCl (pH 7.4), 1 mM EDTA (pH 8.0), 300 mM NaCl, 50% formamide, 10% dextran sulphate, 1×Denhardt's 25 mg/ml yeast tRNA, 100 µg/ml salmon sperm DNA, 250 µg/ml total yeast RNA (fraction XI, Sigma), 150 mM DTT, 0.15% sodium thiosulfate (NTS) and 0.15% SDS. Following washes, slides were apposed to Kodak Hyperfilm Biomax MR for 2 days, after which they were coated with nuclear track emulsion (NTB, Kodak). Slides were exposed for 4 weeks at 4° C., after which they were developed in Dektol (Kodak), fixed and counterstained with a Giemsa stain.

Results

Figure 8:
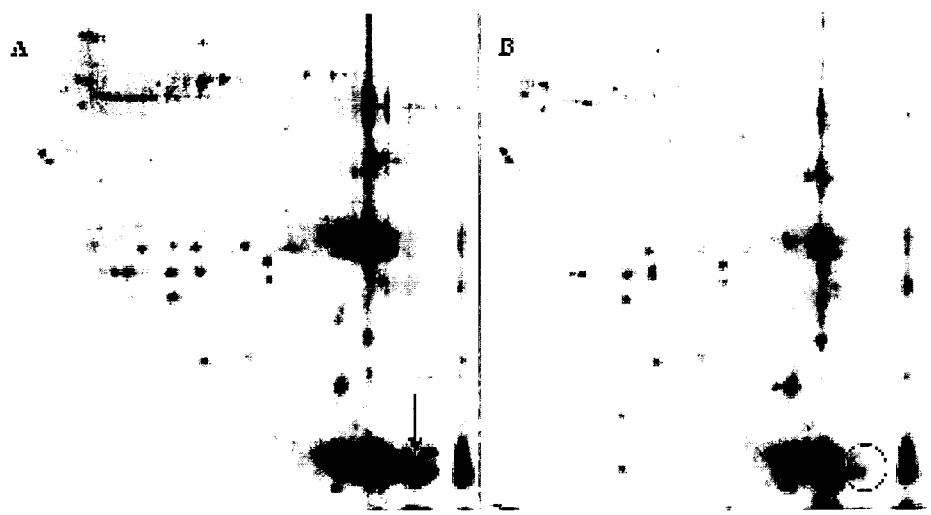
FIG. 8 shows representative gel-images for Hbδ. A) PE sample where the Hbδ-spot is clearly visible (arrow). B) Gel from a control sample where the Hbδ spot is missing (circle).

The extracted placenta proteins were separated by 2D-PAGE to study differences in protein expression between patients with PE and healthy controls. In the first experimental set up, 400 μg of the samples were loaded to the IPG-strip and the second dimension was run using the Hoefer DALT gel apparatus. Only one spot was significantly differently displayed between the two groups. In order to identify the spot, 800 μg of samples were loaded on the gels, and a total of four samples were run, two PE and two control samples. For qualitative analysis the second dimension was run. In doing so, a second differentially expressed spot was detected by the naked eye in the PE samples (FIG. 8). The two protein spots of interest were punched out from the gels, enzymatically digested and identified using MALDI-TOF MS. The first protein was identified as transferrin and the second as haemoglobin.

Figure 9:
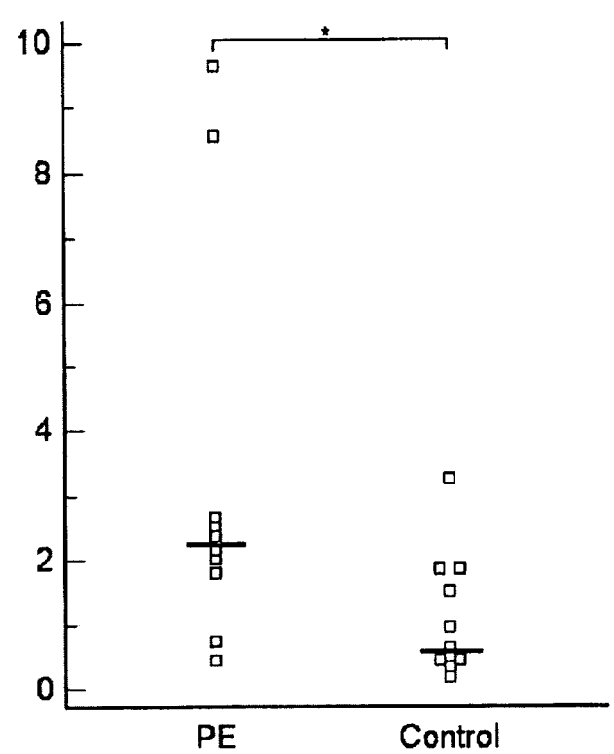
FIG. 9 shows Hbδ mRNA values in placenta quantified with qPCR presented in a scatter-plot.

It was not possible to establish the sub class of haemoglobin with the MALDI data. Therefore this spot was further subjected to sequence analysis using MS-MS analysis. The MS-MS data showed that the obtained sequences belonged to the delta chain of haemoglobin (Hbδ). In agreement with the protein-analysis, real-time PCR also showed a significantly increased gene expression for Hbδ in the PE placentas ($p=0.04$) vs. controls (FIG. 9).

Figure 10:
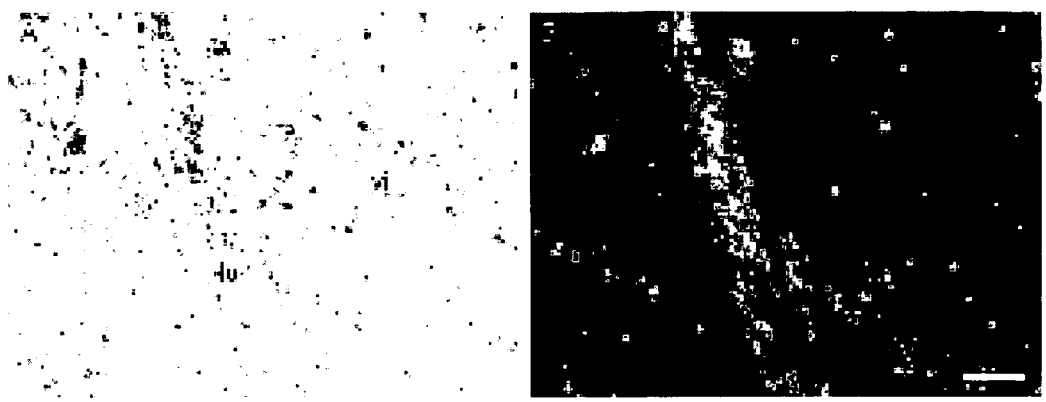
FIG. 10 shows in situ images from a preeclamptic placenta expressing Hbδ mRNA.

In situ hybridization showed single cells expressing Hbδ mRNA throughout the intra-villous space. Hbδ mRNA-expressing cells were particularly seen in and around placenta blood vessels. PE placentas appeared to have more scattered cells outside the vessels expressing Hbδ mRNA than controls. No signal was detected in the trophoblasts cells. The cell morphology of the Hbδ expressing cells was concealed by the silver grains overlaying the positive cells (FIG. 10).

Discussion

Our current findings support placental haematopoiesis, by here demonstrating increased expression of HM-protein, as well as corresponding gene expression, in PE.

In the placenta, increased levels of Hbδ mRNA translate into protein which we here show to be accumulated in the PE placenta. However, it is not certain that the Hb chains being produced are arranged into functional Hb molecules with bound porphyrine rings and Fe-ion. Transport and cellular uptake of iron is facilitated by transferrin (TF). Our 2D-gels here also show that the PE placenta is deprived of intracellular TF. This lack of TF protein in the PE placenta may reflect an impaired iron transport into the cell population expressing Hbδ. Thus, cells producing Hb might therefore be deficient in their iron supply, leading to accumulation of Hb chains and/or dysfunctional Hb molecules in the PE placenta. Interestingly, there was no accumulation of haemoglobin in the control placentas even though in situ hybridization showed mRNA expression for Hbδ. The healthy placenta may, in contrast to the PE placenta, be able to regulate the production of Hb either by regulation of mRNA translation, protein degradation, or by simply being an extramedullary site of hematopoiesis. Defect Hb synthesis may lead to defect erythroblasts, theses would then be less resistant and fall apart easier, which in turn leads to more free Hb.

EXAMPLE 4

Detection of HLA-DPA1 RNA Expression

Quantitative RT-PCR was performed to analyze HLA-DPA1 RNA expression.

Sample collection; tissue sampling and handling; RNA extraction; and real-time PCR amplification was performed as described in Example 1 with necessary modifications.

Results

Major histocompatibility complex, class II, DP alpha 1 (HLA-DPA1) was significantly upregulated in the group with notching compared to all other groups ($p=0.01$ against PE without notching, $p=0.02$ against PE with notching, and $p=0.01$ against control) (see FIG. 4D).

Discussion

Women diagnosed with notching have a higher risk of developing PE later on in their pregnancies. However, the fact that not all women with notching develop PE implies that they may express genes that protect or repress genes that harm them. Both microarray and qPCR showed increased expression of HLA-DPA1 in the notch group vs. all other groups. HLA-DPA1 is part of the class II major histocompatibility complex (MHC) family, members of which are responsible for presenting foreign antigens as part of the adaptive immune response. Only class I MHC molecules, HLA types G and E, are expressed on trophoblast cells. They are thought to alter the maternal immune response at the fetal-maternal interface, protecting the fetus from a maternal immune response. Thus HLA-DPA1, a MHC class II molecule, may not be made by trophoblasts. Instead, it may be a maternal reaction to the presence of fetal cells in the placenta.

Fetal cells are known to enter the maternal circulation during pregnancy, and their levels increase in the course of a normal pregnancy suggesting a continuous flow of fetal cells across the placental barrier and into the maternal system. In PE, the number of fetal cells in the maternal circulation is increased vs. normotensive pregnancies. As noted above, the increased expression of HLA-DPA1 in the notch group suggests that the maternal immune system may be reacting to "foreign" antigens in the placenta, specifically, the fetal cells there. Thus, HLA-DPA1 may contribute to the construction of an immunological barrier that prevents fetal cells from entering the maternal systems by identifying the cells and tagging them for destruction. Should the Hb-expressing cells seen in our experiments be of fetal origin, HLA-DPA1 may also prevent these cells from leaking into the placenta, thereby protecting the placenta from excess production of hemoglobin and free heme.

EXAMPLE 5

Haemoglobin and $\alpha_1$-Microglobulin Concentrations in Plasma and Urine, Antioxidation by $\alpha_1$-Microglobulin and In Vitro Placenta Perfusion Materials and Methods Haemoglobin Haemoglobin was purchased from Sigma. Oxyhaemoglobin-A was prepared at our laboratory as follows. Red blood cells from 50 ml human blood were isolated by centrifugation (1200×g, 10 minutes) and washed 4 times with 10 volumes of phosphate buffered saline (PBS, 10 mM phosphate, pH 7.4; 120 mM NaCl and 3 mM KCl). The blood cells were then lysed by resuspension in hypotonic buffer (20 volumes $H_2O$:1 volume PBS) on ice. The membranes were separated from the cytosol by centrifugation (14000×g, 20 minutes) and the supernatant was dialysed 3 times against 15 mM Tris-HCl, pH 8.0 in 4° C. Two-hundred ml of DEAE-Sephandex A-50 (Amersham Biosciences AB, Uppsala, Sweden) was packed in a column and the dialysed supernatant was applied to the gel and separated by a gradient consisting of 15 mM Tris-HCl, pH 8.0 and 15 mM Tris-HCl, pH 8.0+0.2 M NaCl. Fractions were collected and the absorbance was measured at 280 nm, 577 nm and 630 nm to identify and determine the concentration of oxyhemoglobin-A. Oxyhemoglobin F was prepared from human chord blood using the same protocol.

Proteins and Antibodies

Recombinant human $\alpha_1$-microglobulin ($\alpha_1 m$) was expressed in *E. coli*, purified and refolded as described [Kwasek et al., 2007]. Rabbit anti-mouse immunoglobulin, rabbit anti-hemoglobin and swine anti-rabbit immunoglobulin-alkaline phosphatase (ALP) were purchased from Dako (Denmark). Mouse monoclonal anti-hemoglobin gamma chain antibody was purchased from Santa Cruz Biotechnologies Inc (cat no. sc-21756). Rabbit anti-human $\alpha_1 m$ and goat anti-rabbit immunoglobulin were prepared as described, respectively [Elbashir et al. 1990, Björck et al. 1977]. Monoclonal mouse antibodies against human $\alpha_1 m$ (BN11.10) were prepared as described [Babiker-Mohamed et al., 1991].

Labelling with Iodine

Proteins were labelled with $^{125}I$ (Bio-Nuclear AB, Stockholm, Sweden) using the chloramin-T method [Greenwood et al, 1963]. The labelled proteins were separated from free iodide by gel filtration on Sephadex G-25 column (PD-10, GE Healthcare). The specific activities were approximately 0.3 MBq per µg protein for $\alpha_1 m$ and 0.5 MBq per µg protein for immunoglobulins.

Patients and Sampling

Placenta and blood samples were collected from women admitted to Lund University Hospital (30 controls, 30 PE). Sampling was performed with written consent and was approved by the Swedish Ethical Committee Review Board. Preeclampsia was defined as a blood pressure above 140/90 mmHg and proteinurea above 0.3 g/L {Milne, 2005 #89}. Only patients with bilateral notching were sampled for the group with notching without PE. A 10×10×10 mm cube of villous tissue was removed after delivery and immediately put on dry ice. Samples were stored at −80° C. until usage. Blood samples were collected before delivery and stored using Paxgene Blood RNA System (Qiagen, Valencia, USA) at −20° C. until usage. Various parameters of these groups are described in Table 2, page 37-38. In addition, samples from the 10 patients and 10 control subjects of the Tanzania study were investigated in Examples 5 (see Table 1, page 14-15).

ELISA

Haemoglobin-A concentrations were measured using competetive enzyme-linked immunosorbent assay (ELISA) as described for solid phase phase radioimmunoassay (SPRIA) and using buffers, washing procedure and incubation times as described [Nilson et al., 1986]. Haemoglobin (Sigma) was coated at 4 µg/ml, plates washed and incubated with a mixture of rabbit anti-haemoglobin and either standard oxyhaemoglobin-A or unknown samples, washed, incubated with swine-anti-rabbit IgG-ALP (Dako), washed and finally incubated with substrate. Appropriate dilutions of each step and reagent were titrated separately. Absorbance was read at 415 nm (Bio-Rad Model 550, Microplate reader). The volume used for every incubation step was 100 µl. All experiments were made in triplicates.

RIA $\alpha_1 m$ concentrations were determined by radioimmunoassay (RIA) as described [Plesner et al. 1975; Åkerström, 1985]. Briefly, goat antiserum against human $\alpha_1 m$ (0.2 ml, dil. 1:6000) was mixed with $^{125}I$-labelled $\alpha_1 m$ (0.1 ml, appr. 0.05 pg/ml) and unknown samples or standard $\alpha_1 m$-concentrations (0.2 ml). The dilutions were done in 0.1M sodium phosphate, pH 7.5+0.1% BSA (RIA buffer). After incubating overnight at room temperature, antibody-bound $\alpha_1 m$ was precipitated by adding 0.3 ml bovine serum and 1.6 ml 15% polyethylene glycol in RIA-buffer, centrifuging at 1500×G for 40 min, and analysing the $^{125}I$-activity of the pellets in a Wallac Wizard 1470 gamma counter (Perkin Elmer Life Sciences).

Determination of Hb-F Concentrations

The plasma concentrations of haemoglobin F were determined by Western blotting after removal of plasma albumin using Montage Albumin Deplete Kit (cat no. LSKAD0024; Millipore). Briefly, the beads from ten columns were pooled into one batch, washed with PBS and separated into 50 identical aliquots. After centrifugation, the supernatant of each aliquot was discarded and 40 µl plasma (diluted 1:1 with PBS) added and incubated twice for 1 h at RT. The tubes were centrifuged, the supernatant saved and the beads washed with sequentially with 1 ml 0.1M glycin-HCl, pH 2.3 and 1 ml 0.1M Tris-HCl, pH 8. After centrifugation and removal of the supernatant, the plasma was added and incubated again for 1 h at RT. After centrifugation and discarding the pellet, 10 µl of the thus albumin-depleted plasma was separated by SDS-PAGE (T=13.5%; C=3.3%) and blotted with mouse anti-human Hb-F/γ-chain, diluted 600×, followed by rabbit anti-mouse Ig (1 µg/ml) and the 125I-labelled goat anti-rabbit IgG as described below. Quantification of haemoglobin F was achieved by densitometry of the positive bands using Image Gauge V4.0 software (Fuji, Tokyo, Japan) and standard haemoglobin F (15 and 75 ng/well). Urine concentrations of haemoglobin F were determined using the same protocol, but omitting the steps with Montage Albumin Deplete Kit.

Western Blotting

SDS-PAGE (T=12%, C=3.3%) was performed as described [Laemmli, 1970]. The gels were run under reducing conditions using a high molecular weight standard (Rainbow markers, Amersham Biosciences, Buckinghamshire, England). The separated proteins were transferred to polyvinylidenedifluoride (PVDF) membranes (Immobilon, Millipore, Bedford, Mass., USA) as described [Matsudaira, 1987]. The membranes were then incubated with the appropriate antibodies and Western blot was performed using $^{125}I$-labelled secondary goat anti-rabbit immunoglobulins as previously described by Wester et al [1997], and developing the images on the membranes using Fuji FLA 3000 phosphoimaging system (Fujifilm Sweden AB, Stockholm, Sweden).

Placenta Tissue Extraction and Preparation of $\alpha_1 m$-molecules

Molecules containing $\alpha_1 m$ were purified from placenta tissue as described [Berggård et al., 1999]. Approximately 200 g of an apparently normal term human placenta, taken within 3 hours after delivery, were homogenized in 200 ml of 50 mM Tris-HCl, pH 8.0, 0.25 M sucrose, 2 mM EDTA, pepstatin, 1 mg/l, antipain, 5 mg/l, and leupeptin, 10 mg/l, using a Potter-Elvehjem apparatus with a tight-fitting teflon pestle. The homogenate was centrifuged at 10,000 G for 10 min. This pellet was washed by repeatedly suspending 1:1 in the homogenization buffer and recentrifugation at 10,000 G for 10 min. The supernatant was centrifuged at 100,000 G for 90 min. This pellet, containing the placenta membranes and membrane-bound proteins, was dissolved in 40 ml homogenization buffer also containing 0.5% (w/v) Nonidet P-40 (BDH Chemicals) and centrifuged at 20,000 G for 30 min to remove particulate material. All steps were performed on ice or at 4° C. Immunosorbent affinity chromatography was done with monoclonal mouse anti-$\alpha_1 m$, BN11.10, immobilized to Affigel Hz (20 mg/ml) according to the manufacturer's instructions (Bio-Rad Laboratories, Richmond, Calif., USA).

In Vitro Placenta Perfusion

There are up to date no adequate animal models for PE. In order to study the effects of free haemoglobin we are setting up the dual placental perfusion model in collaboration with Henning Schneider, Greifswald, Germany. The dual-placenta perfusion is a well-established model to study the placental blood flow in-vitro [Schneider et al., 1985]. Recently, the model was used to mimic PE by inducing ROS formation with xanthine and xanthine oxidase [Di Santo et al., 2007]. Our very recent data indicate that placentas perfused with xanthine have a gene profile similar to PE placentas.

Human placenta is artificially perfused with an oxygenated media. Both the maternal and fetal circulation is perfused (hence "dual") using peristaltic pumps. The media from the two separated circuits are monitored for leaks. The media and placenta tissue is analyzed with the above mentioned technology.

EXAMPLE 5.1

Hemoglobin-A is Elevated in Preeclamptic Plasma

Results

Figure 11:
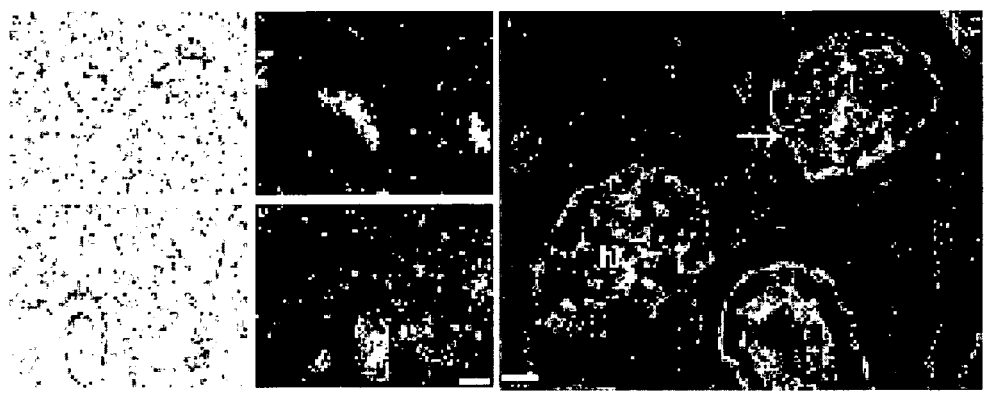
FIG. 11. In situ hybridizations from placenta and placenta bed samples (left panel). Dark field image of haemoglobin mRNA-expression in a representative preeclamptic placenta sample and control. Haemoglobin mRNA expression was especially seen in and around blood vessels (arrow heads). Several scattered cells in the inter-villous space are seen in PE. Immunohistochemistry (right panel) shows accumulation of free fetal haemoglobin (arrow) in the lumen (lu) of the placental vasculature.
Figure 12:
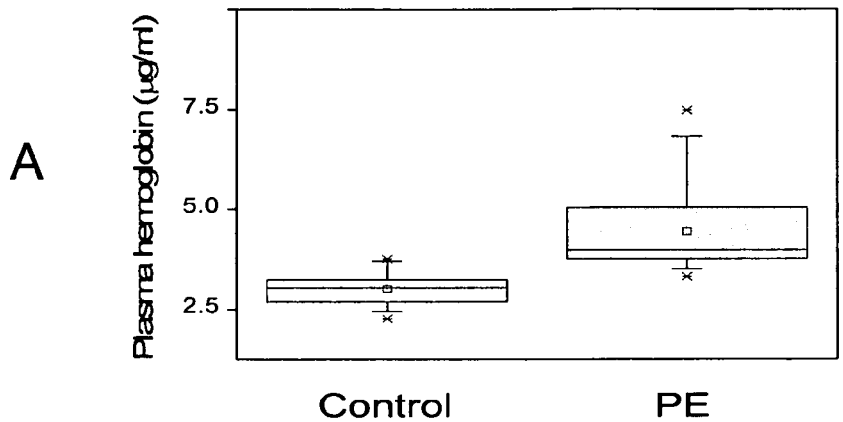
FIG. 12. Total haemoglobin concentrations in plasma from women with preeclamptic pregnancies (n=30) and normal pregnancies (n=30). The concentrations were measured by ELISA using antibodies against adult haemoglobin (Hb-A), diluting the plasma 1000×.
Figure 12:
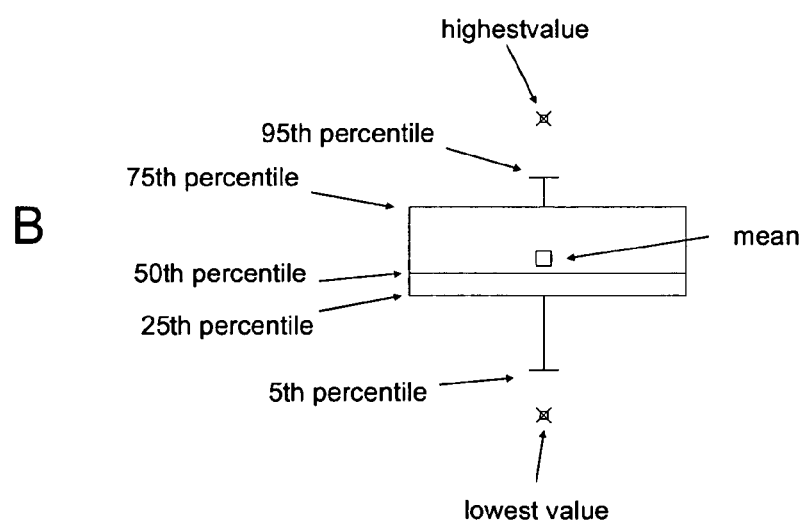

The results are shown in FIGS. 11-12. Determination of the total haemoglobin concentrations in plasma of 30 patients with preeclampsia and 30 control pregnancies by ELISA showed an almost two-fold increase in the preeclampsia group. The mean value +/−SD in the patients was 3.01+/−0.39 ug/ml and in the control group 4.44+/−1.0. This difference is significant (P<0.05).

EXAMPLE 5.2

Haemoglobin-F is Elevated in Preeclamptic Plasma and Urine

Figure 13:
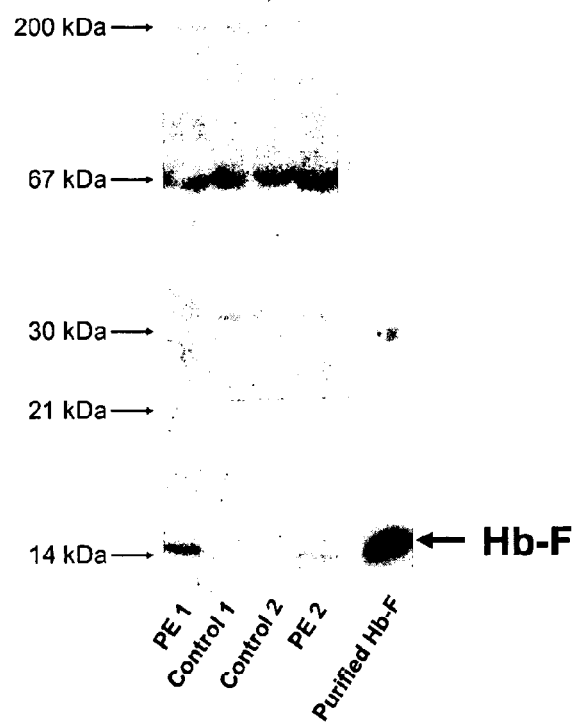
FIG. 13. Determination of Hb-F by Western blotting in plasma from two patients with preeclampsia (PE 1 and 2) and two control individuals with normal pregnancies (Control 1 and 2). The plasma samples were treated with albumin-extraction beads as described and then applied (15 µl), non-diluted, to the SDS-PAGE/Western blotting procedure. To allow estimation of concentrations in µg/ml, 0.1 µg purified Hb-F was applied in a separate lane ("Purified Hb-F").
Figure 14:
FIG. 14. The fetal circulation with hemoglobin synthezising cells (white ovals with a black dott). Due to damage to the placenta barrier, fetal cells are leaking into the intervillous space and thereby the maternal circulation FIG. 15. Total $\alpha_1 m$ concentrations in plasma from women with preeclamptic pregnancies (n=30) and normal pregnancies (n=30). The concentrations were measured by RIA, diluting the plasma 500×.

Fetal haemoglobin in plasma and urine was seen with Western blotting as a 15 kDa-band reacting with anti-gamma chain. FIG. 13 shows an example of the Western blotting method applied to plasma of two patients (PE 1 and 2) and two control subject (Control 1 and 2). The detection limit of the method was approximately 5 μg/ml in plasma and 1 ug/ml in urine. The concentrations of Hb-F were estimated by densitometry and Table 1 shows the frequencies of Hb-F in the plasma and urine samples from the PE and control groups. The band was seen in the plasma of 9 patients, whereas none of the control individuals were positive. Thus, 9 patients and no control women had more than 5 μg/ml fetal haemoglobin in plasma. Assuming that the plasma concentrations of the control 10 women were 0.04 ug/ml as the study of Turpeinen et al. [1992] suggests, i.e. the normal plasma concentration, our results show a 125-fold increase of fetal haemoglobin in 20% of the patients with PE. Urine of 8 patients contained the band and 2 of the controls (Table 3). These two control individuals were found among the Tanzania women, with high incidence of malaria infections. A weakly positive band at 67 kDa, most likely representing albumin was seen at equal intensity in all samples.

TABLE 3

Frequencies of individuals with >5 μg/ml Hb-F in plasma and >1 μg/ml in urine.

| Plasma | | Urine | |
| --- | --- | --- | --- |
| Preeclampsia % | Control % | Preeclampsia % | Control % |
| 19.6 (9/46) | 0 (0/39) | 20 (8/40) | 5 (2/39) |

EXAMPLE 5.3

Time-Dependence of Plasma Haemoglobin-A and F

A possible early pathogenic factor of preeclampsia is hypoxia, caused for example by faltering perfusion, abnormal implantation or starvation. Hypoxia can upregulate Hb-F expression in both fetal and adult haematopoietic stem- and progenitor cells [Narayan et al., 2005]. Together with injury on the physical barriers of the placenta, this may lead to leakage of fetal cells as well as free Hb-F into the maternal circulation between stage 1 and 2 (see FIG. 15). As the disease progresses, the number will increase which can be monitored as increased free fetal haemoglobin levels. When the maternal vascular walls are damaged by free fetal haemoglobin, the maternal blood cells will also begin to die. This will lead to increased levels of free maternal haemoglobin, driving the negative spiral of disease further. The hypothesis is that Hb-F precedes total Hb.

EXAMPLE 5.4

$\alpha_1$m is Elevated in Preeclamptic Plasma and Urine

The small plasma and tissue protein $\alpha_1$-microglobulin ($\alpha_1$m) is a heme-binder [Allhorn et al., 2002; Larsson et al., 2004] and radical scavenger [Åkerström et al. 2007] and a heme-degrading form, t-$\alpha_1$m, is induced by proteolytic removal of a C-terminal tetrapeptide, LIPR when $\alpha_1$m is mixed with free haemoglobin [Allhorn et al., 2002]. Free haemoglobin and reactive oxygen species causes an increased production of $\alpha_1$m in liver cells and blood cells [Allhorn et al., 2002]. Therefore, $\alpha_1$m is a potential heme- and haemoglobin antagonist that can protect against heme- and ahemoglobin-induced damage to cells and tissue components.

Figure 15:
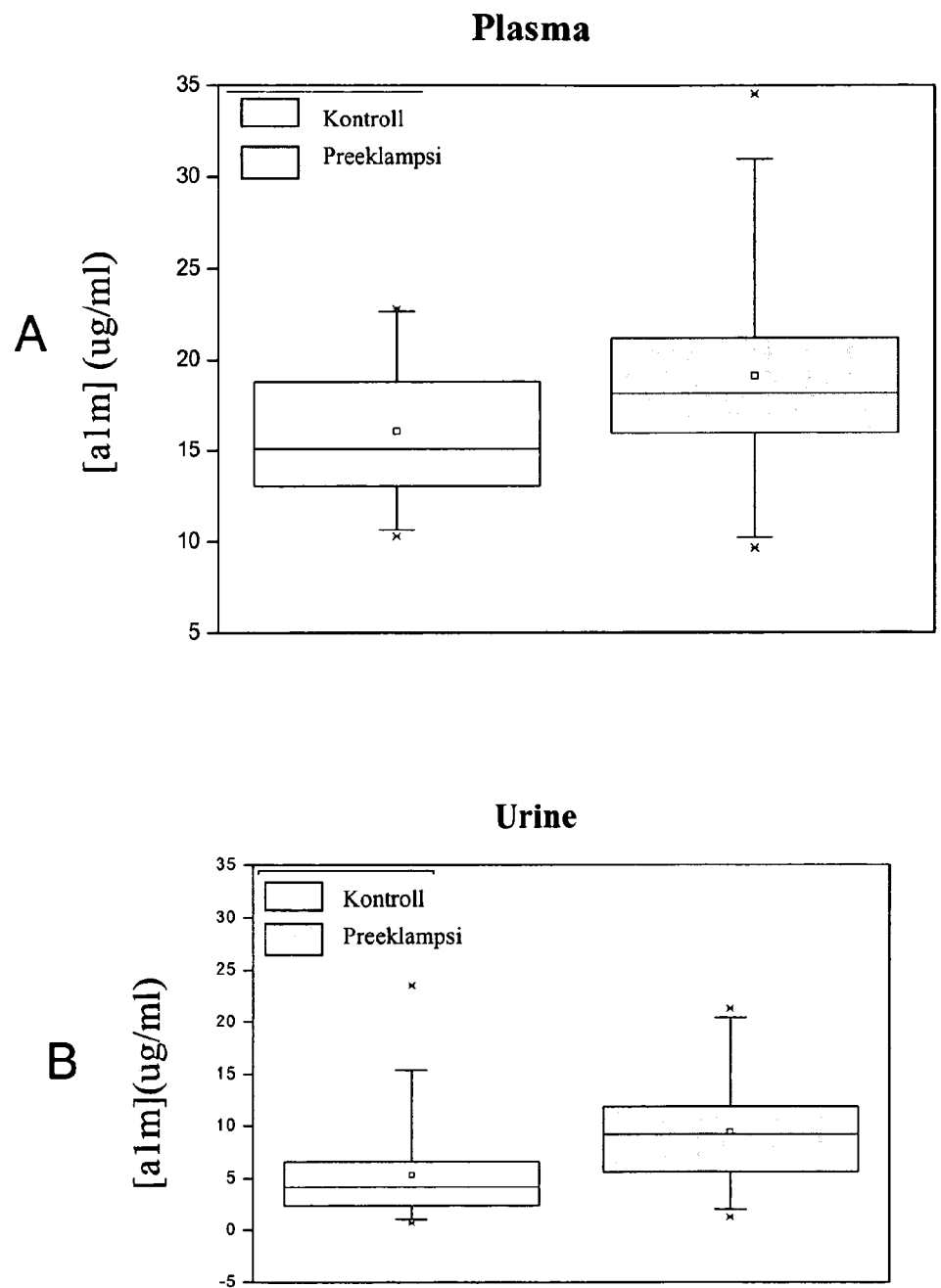

In concert with this hypothesis, we have found that the concentrations of $\alpha_1$m are elevated in plasma and urine from patients with preeclampsia compared to control pregnancies with a significance of P<0.01 in both plasma and urine (FIG. 15). The mean plasma $\alpha_1$m-concentration (+/−SD) in patients was 19.1 (+/−5.5) ug/ml and in controls 16.1 (+/−3.7) μg/ml. The mean urine $\alpha_1$m-concentration (+/−SD) in patients was 9.4 (+/−5.5) μg/ml and in controls 5.3 (+/−4.6) μg/ml. These results indicates 1) that the body responds to the preeclamptic insult by increasing the production of $\alpha_1$m thus elevating the plasma concentration and 2) that haemoglobin, heme, iron and/or ROS are components of the insult since $\alpha_1$m is up-regulated in cells by increased haemoglobin, heme, iron and/or ROS. Therefore, $\alpha_1$m most likely is a defence reaction of the body against the preeclamptic insult. Consequently, increasing $\alpha_1$m concentrations to even higher levels, for example 32 μg/ml, which is twice the normal concentration, should have anti-preeclamptic effects, and $\alpha_1$m is therefore a potential drug for treatment of the disease.

EXAMPLE 5.5

Figure 16:
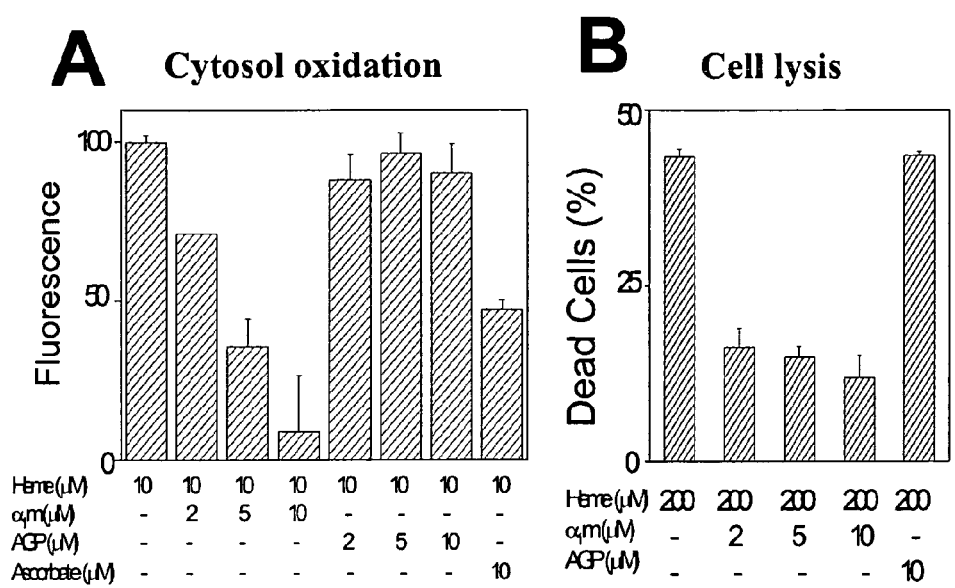
FIG. 16. A. Cell-protective properties of $\alpha_1 m$ against heme- and ROS-induced oxidation. K562 cells were labelled with the oxidation-sensitive probe $H_2 DCFDA$, washed, and incubated with $\alpha_1 m$ (2, 5 or 10 µM), AGP (2, 5 or 10 µM) or ascorbate (10 µM) prior to the addition of 10 µM heme. The cells were incubated for 2 h and analysed with FACS. B. K562 cells were cultured with $\alpha_1 m$ (2, 5 or 10 µM) or a control protein ($\alpha_1$-acid glycoprotein, AGP) (10 µM) prior to the addition of 200 µM heme and cultured 4 h. The cell suspension was collected, mixed with propidium iodide and analysed with FACS.
Figure 17:
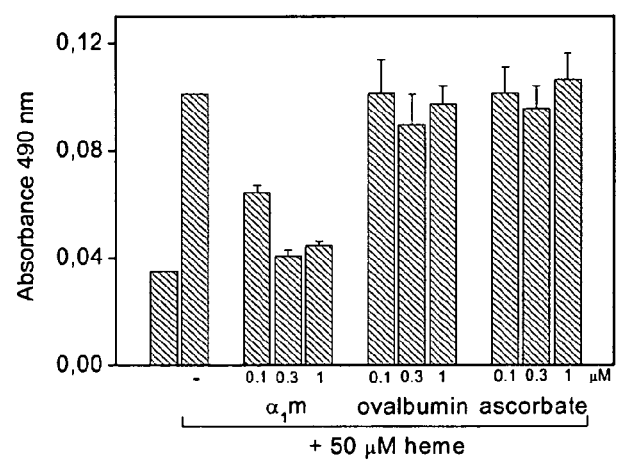
FIG. 17. Reduction of carbonyl groups on oxidized collagen by $\alpha_1 m$. Collagen, coated to microtiter plates, was oxidized by incubation with 50 μM heme for 17 h. After washing, 0.1, 0.3 or 1 μM $\alpha_1 m$, ovalbumin or ascorbate were added, and incubated for 2 h. Carbonyl groups were measured by ELISA. Each column represents the mean of triplicates +/−SE FIG. 18. Scavenging of cell heme by $\alpha_1 m$. Human erythroleukemic cells (K562) were cultured with either buffer or 10 μM heme for 30 minutes, washed and resuspended in fresh culture medium. A: The cells were then incubated with $\alpha_1 m$ (2 or 10 μM) for 2 hours, after which time the culture medium was saved. The cells were washed and solubilized by suspending in a buffer containing 1% NP-40. The culture medium and cellsuspension were then analysed spectrophotometrically by reading the absorbance spectra (300-700 nm). B: The various cultures were also analysed visually. Cells were incubated with either buffer or 10 μM heme for 30 min (Step 1), washed and then incubated with buffer, 10 μM $\alpha_1 m$ or 10 μM AGP for 2 hours (Step 2), washed and solubilized as described above.

$\alpha_1$m Protects Cells and Tissue Components by Anti-Oxidation and Heme-Binding The anti-oxidation properties of $\alpha_1$m are illustrated in FIGS. 16 and 17. First, it was shown that extracellularly added $\alpha_1$m can reduce the redox charge of cell cytosol and cytosol protein thiol groups, and inhibit the oxidation of these components by heme and ROS. Extracellularly added $\alpha_1$m also inhibits the cell lysis (i.e. cell death) induced by heme (FIG. 16). Oxidative modification of collagen and low-density lipoproteins (LDL) is involved in the pathogenesis of many diseases and may also be targets of Hb-induced oxidation in preeclampsia. $\alpha_1$m inhibited heme- and ROS-induced oxidation of collagen, LDL, membrane lipids and whole cells. $\alpha_1$m also removed pre-formed oxidation products on collagen and LDL (FIG. 17). A possible mechanism for these actions may be the reductase properties of $\alpha_1$m, reducing the oxidants, the oxidation modifications, or both.

Figure 18:
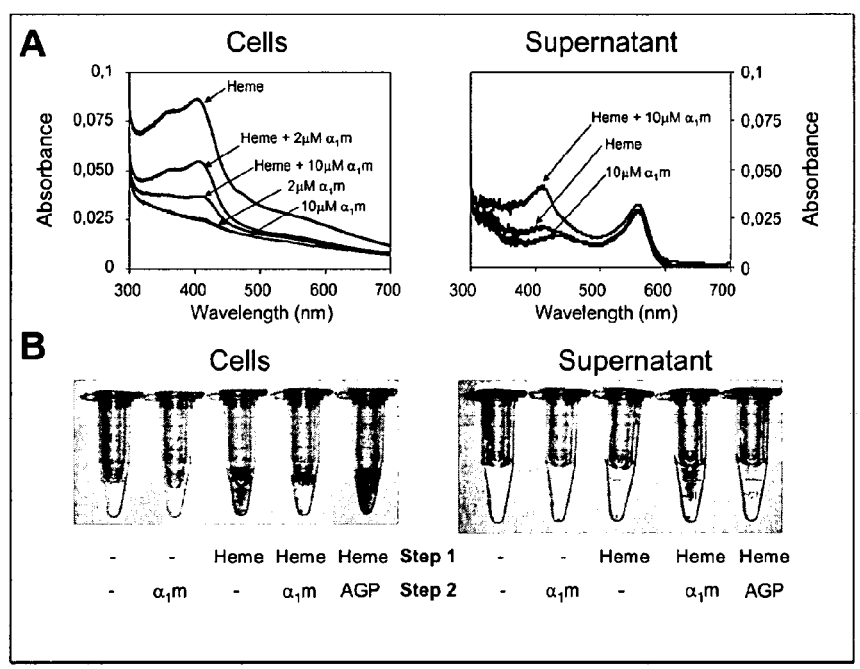

To study the mechanisms of the cytoprotective effect of $\alpha_1$m, we performed a series of experiments attempting to analyze the interactions between the protein and cell-bound heme. First, cells were incubated with 10 µM heme for 30 minutes, excess heme washed off and $\alpha_1$m or control proteins added to a concentration of 2 or 10 µM and incubated for 2 h. The culture media were saved, cells washed and solubilized, and both media and solubilized cells analyzed by spectrophotometry (FIG. 18A) and visually (FIG. 18B). Heme was seen as a strong brown-coloring of the cells and the typical absorbance spectrum with a non-distinct peak around 400 nm. When adding $\alpha_1$m, the heme was almost completely removed from the cells and instead found in the medium. The control lipocalin AGP did not have any effect on the cell-bound heme. We expect that the levels of free heme in preeclampsia can reach 10 µM and above, at least locally, and that the cells affected by the toxic effects of free heme include endothelial cells lining the blood vessels.

As described at several occasions above, oxidative insults by free haemoglobin, free heme and ROS produced by autooxidation of haemoglobin and heme are believed to constitute major pathological factors of the progress of preeclampsia. Collagen and endothelial cell membranes and cytosols are of course important targets of the oxidative insults. The results in this example makes it probable that $\alpha_1$m can inhibit and repair the damage done by free haemoglobin, heme and ROS also in vivo, and therefore can act as an therapeutic agent in preeclampsia.

EXAMPLE 5.6

Figure 19:
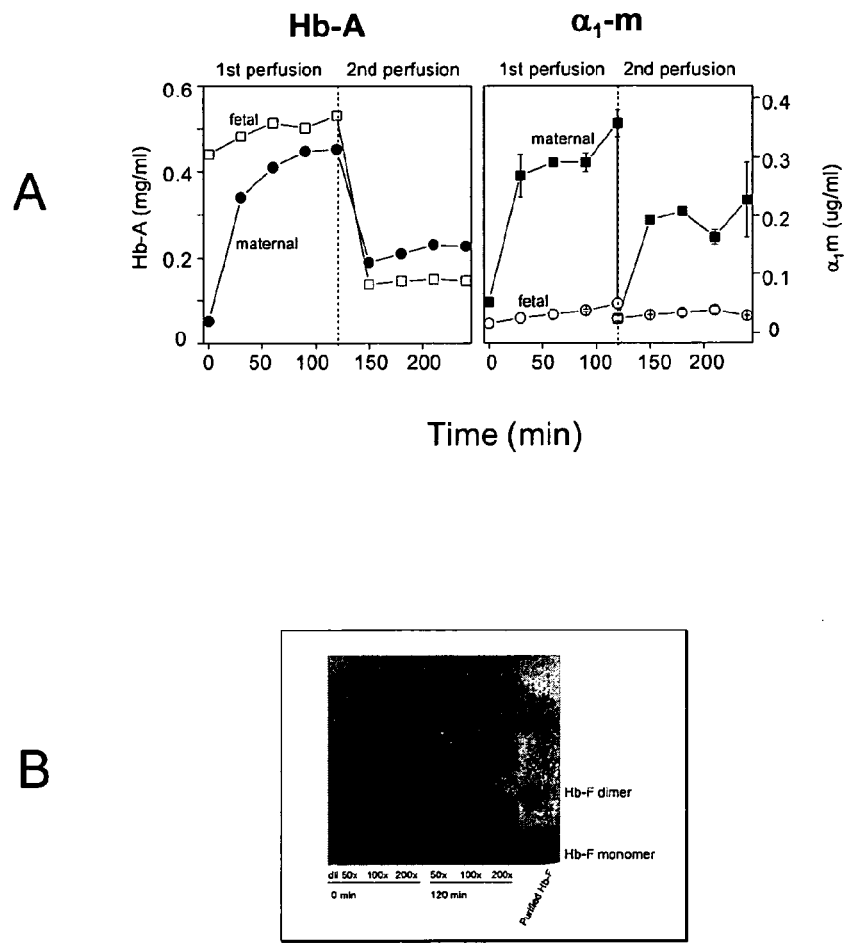
FIG. 19 shows in vitro perfusion of a "healthy" placenta for 120 min with a Hb-A solution (2 mg/ml) on the fetal side (empty symbols) and buffer only for on the maternal side (filled symbols) ("$1^{st}$ perfusion") and for 120 min on both sides with buffer only ("$2^{nd}$ perfusion"). Samples were taken regularly and the concentrations of Hb-A measured by ELISA (left diagram), of $\alpha_1 m$ with RIA (right diagram) and of fetal Hb-A with Western blotting (right photo).

In Vitro Perfusion with Haemoglobin Induces Placenta Leakage and $\alpha_1$m-Upregulation Preeclampsia was studied using an in vitro placenta perfusion model with two separate circulation systems, on the fetal and maternal sides, respectively. Both circulation systems were first rinsed. The placenta was then perfused for 120 min with a Hb-A solution (2 mg/ml) on the fetal side and buffer only for on the maternal side 120 min ("$1^{st}$ perfusion") and for 120 min on both sides with buffer only ("$2^{nd}$ perfusion"). Small aliquots were taken regularly from both circulations and the concentrations of Hb-A, Hb-F and $\alpha_1$m measured. As shown in FIG. 19 (left side), Hb-A quickly appeared on the maternal side during the $1^{st}$ perfusion and, to a smaller extent, during the $2^{nd}$ perfusion. This could be the result of leakage or endogenous production of Hb-A in the placenta tissue, or both. $\alpha_1$m also appeared on the maternal side during both perfusion periods FIG. 19 (right side). This suggests that $\alpha_1$m is produced in the placenta tissue as a result of the haemoglobin perfusion. Finally, Hb-F appeared in the maternal circulation at the end of the $1^{st}$ perfusion (120 min), most likely as a result of production in the placenta and leakage into the maternal circulation.

Thus, the in vitro perfusion model can therefore be used to study the effect of free haemoglobin in the fetal circulation on the placental barrier function, the protective effects of $\alpha_1$m and the protective cellular response of the tissue.

EXAMPLE 5.7

Figure 20:
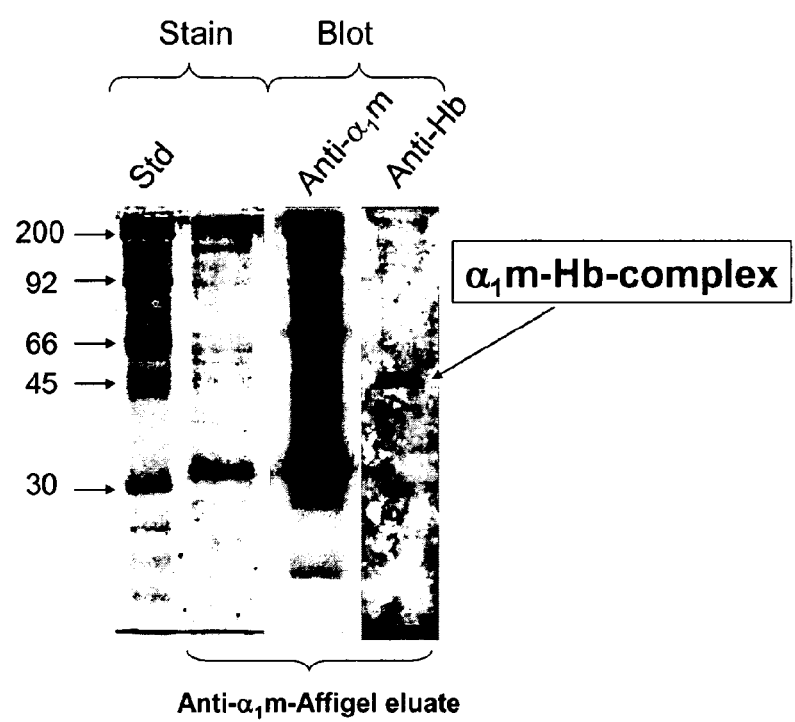
FIG. 20 show SDS-PAGE and Western blotting of a haemoglobin-$\alpha_1 m$ complex isolated from placenta tissue. A placenta from a healthy donor was homogenized and centrifuged at 100,000 G for 60 min. The supernatant was applied to an anti-$\alpha_1 m$ Affigel column which was rinsed and eluted with 0.1M glycine-HCl, pH 2.3. The eluate was separated by SDS-PAGE which was either stained with Coommassie (two left lanes) or transferred to PVDF membranes and blotted with anti-$\alpha_1 m$ or anti-Hb-A.
Figure 21:
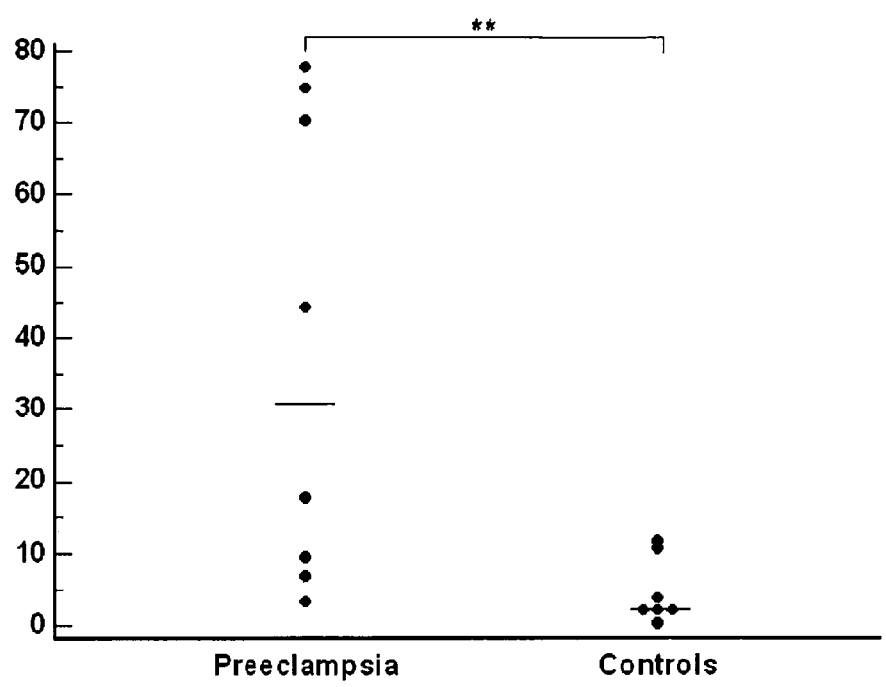
FIG. 21 shows the result from the Tanzania study. Total haemoglobin (μg/ml) in urine before delivery is shown.

A New Molecule in Placenta Consisting of $\alpha_1$m and Haemoglobin Bound to Each Other It was shown previously that $\alpha_1$m can "steal" the heme-group from haemoglobin when mixing the two molecules in solution [Allhorn et al., 2002; Larsson et al., 2004]. To achieve this in vivo, the haemoglobin and $\alpha_1$m molecules should must to each other. Evidence of such an $\alpha_1$m-haemoglobin molecule was seen in placenta extracts, after isolation of $\alpha_1$m-containing molecular species, followed by analysis with anti-Hb blotting (FIG. 20). A 43-kDa protein band reacted with antibodies against both $\alpha_1$m and Hb-A. The band was shown by Maldi-MS peptide mapping to contain $\alpha_1$m and both alpha- and beta-globin chains (not shown). The size of the molecule suggests that the molecule is composed of one chain each of $\alpha_1$m and another chain which can be either Hbα or Hbγ. The band could not be seen after addition of mercaptoethanol, indicating that the chains are held together by a disulfide bond.

REFERENCES

Åkerström B. *J. Biol. Chem.* 260 (1985) 4839-4844.
Åkerström B, Maghzal G, Winterbourn C C, Kettle A J. J Biol Chem. 282 (2007) 31493-31503.
Allhorn M, Berggård T, Nordberg J, Olsson M L, Åkerström B. Blood. 99 (2002) 1894-1901.
Babiker-Mohamed H, Forsberg M, Olsson M L, Winquist O, Nilson B H K, Lögdberg L, Åkerström B. Scand J Immunol 34 (1991) 655-666.
Berggård T, Enghild J J, Badve S, Salafia C M, Lögdberg L, Åkerström B. Am J Repr Immunol 41 (1999) 52-60.
Björck L, Cigen R, Berggård B, Löw B, Berggård I. Scand J Immunol 6 (1977)1063-1069. Bradley D J et al. J Neurosci 12 (1992) 2288-2302
J. J. Brosens, R. Pijnenborg, I. A. Brosens, Am J Obstet Gynecol. 187, 1416 (2002).
Coligan J E. (ed) Current Protocols in Immunology. Wiley Interscience.
C. J. M. de Groot, R. N. Taylor, Annals of Medicine 25, 243 (1993).
Di Santo S, Sager R, Andres A C, Guller S, Schneider H. Placenta (2007).
Douglas and Redman, Br Med J 309 (1994)1395-1400
Elbashir M I, Nilson B, Åkesson P, Björck L, Åkerström, B. J Immunol Methods 135 (1990) 171-179.
J. P. Granger, B. T. Alexander, W. A. Bennett, R. A. Khalil, Am J Hypertens. 14, 178S (2001).
Greenwood F C, Hunter W M, Glover J S. Biochem. J, 89 (1963) 114-123.
S. R. Hansson et al., Mol Human Reproduction, (2005).
T. H. Hung, J. N. Skepper, D. S. Charnock-Jones, G. J. Burton, Circ Res 90, 1274 (Jun. 28, 2002).
Kajita A, Taniguchi K, Shukuya K. Biochim Biophys Acta 175 (1969) 41-48.
Kwasek A, Osmark P, Allhorn M, Lindqvist A, Åkerström B, Wasylewski Z. Protein Expr. Purif. 53 (2007) 145-152.
Laemmli U K. Nature 227 (1970) 680-685.
Larsson J, Allhorn M, Åkerström B. Arch Biochem. Biophys. 432 (2004) 196-204.
H. Lipstein, C. C. Lee, R. S. Crupi, Am J Emerg Med. 21, 223 (May, 2003).
Matsudaira P. J. Biol. Chem. 262 (1987) 10035-10038.
Motterlini et al., Am J Physiol 269 (1995) 648-655.
Narayan A D., Ersek A., Campbell T A., Colón D M, Pixley J S, Zanjani E D. Br J Haematol 128 (2005) 562-570.
Nilson B, Björck L and Åkerström B. J Immunol Methods 91 (1986) 275-281.
Noble R W. J Biol Chem 246 (1971) 2972-2976.
Olsson M G, Allhorn M, Olofsson T, Åkerström B. Free Rad Biol Med 42 (2007) 842-851.
E. W. Page, *Am J Obstet Gynecol.* 37, 291 (1939).

Plesner T, Nörgaard-Pedersen B, Boenisch T. Scand J Clin Lab Invest 35 (1975) 729-735.
J. M. Roberts et al., *Am J Obstet Gynecol* 161, 1200 (1989).
J. M. Roberts, C. A. Hubel, *Lancet* 354, 788 (Sep. 4, 1999).
J. M. Roberts, D. W. Cooper, *Lancet* 357, 53 (2001).
Schneider H, Huch A, Contrib Gynecol Obstet 13 (1985) 40.
A. H. Shennan, L. Poston, L. C. Chappell, P. T. Seed, *Lancet* 357, 1534 (2001 May 12, 2001).
J. M. Stevens, *Med J Aust.* 2, 949 (Dec. 20-27, 1975).
H. Strevens et al., *Br J Obstet Gynaecol.* 110, 831 (September 2003)
Svistunenko et al., J Biol Chem 272 (1997) 7114-7121
Turpeinen U, Stenman U-H. Determination of fetal hemoglobin by time-resolved immunofluorometric assay. Clin Chem 38 (1992) 2013-2018.
Winterbourn C C. Oxidative reactions of hemoglobin. Methods Enzymol. 186 (1990) 265-272.

ITEMS (SPECIFIC EMBODIMENTS OF THE INVENTION)

1. Method for the diagnosis or aiding in the diagnosis of preeclampsia comprising the following steps:
   (a) obtaining a biological sample from a pregnant female mammal;
   (b) measuring the level of free fetal haemoglobin or measuring the level of free fetal haemoglobin and the level of total free haemoglobin, in said biological sample; and
   (c) comparing the level of free fetal haemoglobin in the sample with a reference value or comparing the ratio between the level of free fetal haemoglobin and the level of total free haemoglobin in the sample with a reference value, to determine if said pregnant female has or has not preeclampsia, or is or is not at increased risk of developing preeclampsia.
2. Method according to item 1, wherein said reference value is the level of free fetal haemoglobin or the ratio between the level of free fetal haemoglobin and the level of total free haemoglobin, in samples from a control group, wherein a higher level of free fetal haemoglobin or a higher value of said ratio in the sample relative to the reference value indicates that said pregnant female has preeclampsia or is at increased risk of developing preeclampsia.
3. Method according to any one of items 1-2, wherein said biological sample is blood.
4. Method according to any one of items 1-2, wherein said biological sample is urine.
5. Method according to any one of items 1-2, wherein said biological sample is placental tissue.
6. Method according to any one of items 1-5, wherein the level of free fetal haemoglobin is measured by measuring the level of haemoglobin gamma chain (Hbγ) in the sample.
7. Method according to any one of items 1-6, wherein the free fetal haemoglobin level is measured using an immunological assay.
8. Method according to item 7, wherein the immunological assay is an ELISA.
9. Method according to any one of items 1-6, wherein the free fetal haemoglobin level is determined by measuring free fetal haemoglobin RNA.
10. Method according to item 9, wherein free fetal haemoglobin RNA is measured using real-time PCR.
11. Method according to any one of items 1-10, wherein said mammal is a human.
12. Method for monitoring the progression or regression of preeclampsia, comprising:
   (a) measuring the level of free fetal haemoglobin or measuring the level of free fetal haemoglobin and the level of total free haemoglobin, in a first biological sample isolated from a pregnant female mammal;
   (b) measuring the level of free fetal haemoglobin or measuring the level of free fetal haemoglobin and the level of total free haemoglobin, in a second biological sample isolated from said pregnant female mammal at a later time; and
   (c) comparing the values measured in step (a) and (b), wherein an increase in the free fetal haemoglobin level in the second sample relative to the free fetal haemoglobin level in the first sample or an increase in the ratio between the level of free fetal haemoglobin and the level of total free haemoglobin in the second sample relative to the ratio between the level of free fetal haemoglobin and the level of total free haemoglobin in the first sample, indicates preeclampsia progression; and a decrease in the free fetal haemoglobin level in the second sample relative to the free fetal haemoglobin level in the first sample or a decrease in the ratio between the level of free fetal haemoglobin and the level of total free haemoglobin in the second sample relative to the ratio between the level of free fetal haemoglobin and the level of total free haemoglobin in the first sample, indicates preeclampsia regression.
13. Method of assessing the efficacy of a treatment for preeclampsia comprising the following steps:
   (a) measuring the level of free fetal haemoglobin or measuring the level of free fetal haemoglobin and the level of total free haemoglobin, in a first biological sample obtained from a pregnant female mammal before treatment;
   (b) measuring the level of free fetal haemoglobin or measuring the level of free fetal haemoglobin and the level of total free haemoglobin, in a second biological sample from the same pregnant mammal after treatment; and
   (c) comparing the level or the levels determined in (a) with the level or the levels determined in (b), wherein a decrease in the free fetal haemoglobin level in the second sample relative to the free fetal haemoglobin level in the first sample or a decrease in the ratio between the level of free fetal haemoglobin and the level of total free haemoglobin in the second sample relative to the ratio between the level of free fetal haemoglobin and the level of total free haemoglobin in the first sample, indicates that the treatment is efficacious for treating preeclampsia.
14. Assay kit for the diagnosis or aiding in the diagnosis of preeclampsia, according to the method of any one of items 1-11, comprising means for measuring the level of free fetal haemoglobin in a biological sample of a pregnant female mammal and instructions for using said detecting means.
15. Assay kit according to item 14, wherein the level of free fetal haemoglobin is measured by measuring the level of haemoglobin gamma chain (Hbγ).
16. Assay kit according to any one of items 14-15, which further comprises means for detecting the level of total free haemoglobin.
17. Method for the diagnosis or aiding in the diagnosis of preeclampsia comprising the following steps:
   (a) obtaining a biological sample from a pregnant female mammal;
   (b) measuring the level of free haemoglobin or measuring the level of a free haemoglobin subunit and the level of total free haemoglobin, in said biological sample; and (c) comparing the level of free haemoglobin in the sample with a reference value or comparing the ratio between the level of the free haemoglobin subunit and the level of total free haemoglobin in the sample with a reference value, to determine if said pregnant female has or has not preeclampsia, or is or is not at increased risk of developing preeclampsia.

18. Method according to item 17, wherein said reference value is the level of free haemoglobin or the ratio between the level of the free haemoglobin subunit and the level of total free haemoglobin, in samples from a control group, wherein a higher level of the free haemoglobin or a higher value of said ratio in the sample relative to the reference value indicates that said pregnant female has preeclampsia or is at increased risk of developing preeclampsia.

19. Method according to any one of items 17-18, wherein said biological sample is blood.

20. Method according to any one of items 17-18, wherein said biological sample is urine.

21. Method according to any one of items 17-18, wherein said biological sample is placental tissue.

22. Method according to any one of items 17-21, wherein the level of free haemoglobin is measured by measuring the level of haemoglobin alpha chain (Hbα), haemoglobin beta chain (Hbβ), haemoglobin delta chain (Hbδ), haemoglobin gamma chain (Hbγ) and/or total free haemoglobin, in the sample.

23. Method according to any one of items 17-22, wherein the free haemoglobin level is measured using an immunological assay.

24. Method according to item 23, wherein the immunological assay is an ELISA.

25. Method according to any one of items 17-22, wherein the free haemoglobin level is determined by measuring free haemoglobin RNA.

26. Method according to item 25, wherein free haemoglobin RNA is measured using real-time PCR.

27. Method according to any one of items 7-26, wherein said mammal is a human.

28. Method for monitoring the progression or regression of preeclampsia, comprising:
(a) measuring the level of free haemoglobin in a first biological sample isolated from a pregnant female mammal; and
(b) measuring the level of free haemoglobin in a second biological sample isolated from said pregnant female mammal at a later time, wherein an increase in the free haemoglobin level in the second sample relative to the free haemoglobin level in the first sample indicates preeclampsia progression and a decrease in the free haemoglobin level in the second sample relative to the free haemoglobin level in the first sample indicates preeclampsia regression.

29. Method according to item 28, wherein the level of free haemoglobin is measured by measuring the level of haemoglobin alpha chain (Hbα), haemoglobin beta chain (Hbβ), haemoglobin delta chain (Hbδ), haemoglobin gamma chain (Hbγ) and/or total free haemoglobin.

30. Method of assessing the efficacy of a treatment for preeclampsia comprising the following steps:
(a) measuring the level of free haemoglobin in a first biological sample obtained from a pregnant female mammal before treatment;
(b) measuring the level of free haemoglobin in a second biological sample from the same pregnant mammal after treatment; and
(c) comparing the level determined in (a) with the level determined in (b), wherein a decrease in the free haemoglobin level in the second sample relative to the free haemoglobin level in the first sample indicates that the treatment is efficacious for treating preeclampsia.

31. Method according to item 30, wherein the level of free haemoglobin is measured by measuring the level of haemoglobin alpha chain (Hbα), haemoglobin beta chain (Hbβ), haemoglobin delta chain (Hbδ), haemoglobin gamma chain (Hbγ) and/or total free haemoglobin.

32. Assay kit for the diagnosis or aiding in the diagnosis of preeclampsia, according to the method of any one of items 17-27, comprising means for detecting, in a biological sample of a pregnant female mammal, levels of free haemoglobin and instructions for using said detecting means.

33. Assay kit according to item 32, wherein the level of free haemoglobin is measured by measuring the level of haemoglobin alpha chain (Hbα), haemoglobin beta chain (Hbβ), haemoglobin delta chain (Hbδ), haemoglobin gamma chain (Hbγ) and/or total free haemoglobin.

34. Use of a composition comprising at least one member selected from the group consisting of haemoglobin binding agents and/or heme binding agents; agents that stimulate haemoglobin degradation and/or heme degradation; and agents that inhibit placental hematopoiesis for the manufacture of a pharmaceutical preparation for the treatment or prophylaxis of preeclampsia.

35. Use of a substance according to item 34, wherein said haemoglobin binding agents and/or heme binding agent is alpha 1-microglobulin.

36. Use of a substance according to item 34, wherein said haemoglobin binding agents and/or heme binding agent is an antibody specific for haemoglobin and/or heme.

37. Method for the treatment or prophylaxis of preeclampsia, which method comprises administering to a subject in need for such treatment or prophylaxis of an effective amount of a pharmaceutical preparation comprising at least one member selected from the group consisting of haemoglobin binding agents and/or heme binding agents; agents that stimulate haemoglobin degradation and/or heme degradation; and agents that inhibit placental hematopoiesis.

38. Method according to item 37, wherein said haemoglobin binding agents and/or heme binding agent is alpha 1-microglobulin.

39. Method according to item 37, wherein said haemoglobin binding agents and/or heme binding agent is an antibody specific for haemoglobin and/or heme.

40. Method of prognosis for preeclampsia comprising the following steps:
(a) obtaining a biological sample from a pregnant female mammal;
(b) measuring the level of human leukocyte antigen DPA1 (HLA-DPA1), in said biological sample; and
(c) comparing the level of HLA-DPA1 in the sample with a reference value.

41. Method according to item 40, wherein steps (a) to (c) are performed to determine if said pregnant female is or is not at increased risk of developing preeclampsia, or is or is not at increased risk of developing a severe form of preeclampsia.

42. Method according to any one of items 40-41, wherein an expression or a high expression of HLA-DPA1 indicates a better prognosis than no expression of HLA-DPA1.

43. Assay kit for the prognosis or aiding in the prognosis of preeclampsia, according to the method of any one of items 40-42, comprising means for detecting, in a biological sample of a pregnant female mammal, levels of HLA-DPA1 and instructions for using said detecting means.

The invention claimed is:

1. A method for diagnosing or aiding in diagnosing preeclampsia in a subject pregnant female comprising the following steps:
   a) determining whether the subject has preeclampsia or is at an increased risk of developing preeclampsia by
      i) measuring the level of free fetal hemoglobin or measuring the level of free fetal hemoglobin and the level of total free hemoglobin in a non-fetal biological sample in the subject, and
      ii) comparing the level of free fetal hemoglobin or the ratio of free fetal hemoglobin and total hemoglobin in the sample to a control value, wherein an increase in the level or ratio in the sample relative to the control is indicative of preeclampsia; and
   b) administering to the subject determined to have preeclampsia or at an increased risk of developing preeclampsia an effective amount of one or more substances selected from the group consisting of haemoglobin binding agents, heme-binding agents, heme-degrading agents and iron-binding agents.

2. The method according to claim 1, wherein the biological sample is selected from the group consisting of a blood sample, a plasma sample, a urine sample and a sample of placental tissue.

3. The method according to claim 1, wherein the free fetal hemoglobin refers to fetal hemoglobin that circulates in a biological fluid.

4. The method according to claim 2, wherein the free fetal hemoglobin refers to fetal hemoglobin that circulates in a biological fluid.

5. The method according to claim 1, wherein the one or more substances are further selected from the group consisting of:
   i) antibodies or fragments thereof of haemoglobin
   ii) haptoglobulin
   iii) CD163
   iv) alpha 1-microglobulin
   v) hemopexin
   vi) heme-oxygenase
   vii) albumin
   viii) transferrin, and
   ix) ferritin.

6. The method according to claim 5, wherein the substance is alpha 1-microglobulin.

* * * * *

UNITED STATES PATENT AND TRADEMARK OFFICE
CERTIFICATE OF CORRECTION

PATENT NO. : 8,568,999 B2  
APPLICATION NO. : 12/526941  
DATED : October 29, 2013  
INVENTOR(S) : Hansson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this
Fifteenth Day of September, 2015

Michelle K. Lee
*Director of the United States Patent and Trademark Office*